United States Patent
King et al.

(10) Patent No.: US 11,234,769 B2
(45) Date of Patent: Feb. 1, 2022

(54) WIRELESS ELECTROMAGNETIC NAVIGATIONAL ELEMENT

(71) Applicant: Lucent Medical Systems, Inc., Kirkland, WA (US)

(72) Inventors: Curtis S. King, Kirkland, WA (US); Steve Vincent, Kirkland, WA (US); Samuel Peter Andreason, Kirkland, WA (US)

(73) Assignee: Lucent Medical Systems, Inc., Kirkland, WA (US)

( * ) Notice: Subject to any disclaimer, the term of this patent is extended or adjusted under 35 U.S.C. 154(b) by 942 days.

(21) Appl. No.: 15/911,003

(22) Filed: Mar. 2, 2018

(65) Prior Publication Data
US 2019/0269466 A1 Sep. 5, 2019

(51) Int. Cl.
*A61B 34/20* (2016.01)
*A61M 5/34* (2006.01)

(52) U.S. Cl.
CPC ............. *A61B 34/20* (2016.02); *A61M 5/343* (2013.01); *A61B 2034/2051* (2016.02); *A61M 2205/3317* (2013.01); *A61M 2205/502* (2013.01); *A61M 2205/8206* (2013.01); *A61M 2207/00* (2013.01)

(58) Field of Classification Search
CPC ........... A61B 34/20; A61B 2034/2051; A61M 5/343; A61M 2205/8206; A61M 2205/3317; A61M 2034/2051; A61M 2205/502; A61M 2207/00; A61M 5/427; A61M 5/345
See application file for complete search history.

(56) References Cited

U.S. PATENT DOCUMENTS

| | | | |
|---|---|---|---|
| 5,425,367 A | 6/1995 | Shapiro et al. | |
| 5,425,382 A | 6/1995 | Golden et al. | |
| 5,622,169 A | 4/1997 | Golden et al. | |
| 5,645,065 A | 7/1997 | Shapiro et al. | |
| 5,767,669 A | 6/1998 | Hansen et al. | |
| 5,775,322 A | 7/1998 | Silverstein et al. | |
| 5,879,297 A | 3/1999 | Haynor et al. | |
| 5,902,238 A | 5/1999 | Golden et al. | |
| 6,129,668 A * | 10/2000 | Haynor ................... | A61B 5/06 128/899 |

(Continued)

OTHER PUBLICATIONS

U.S. Appl. No. 15/820,209, filed Nov. 21, 2017, Connector and Methods for Making and Using the Connector.

(Continued)

*Primary Examiner* — Sanjay Cattungal
(74) *Attorney, Agent, or Firm* — Seed IP Law Group LLP

(57) ABSTRACT

A medical system tracks the position of a portion of a medical instrument within a body of a patient. In some embodiments, the medical instrument includes a needle, a syringe, and a needle-position-tracking element positioned between the needle and the syringe and in fluid communication with both. The needle-position-tracking element includes an electromagnet structure that includes a core, a conductive coil wrapped around the core, and ancillary circuitry configured to pass a current through the conductive coil to thereby generate a magnetic field. A sensor device senses the magnetic field and generates corresponding sensor signals. A control circuit calculates the position of a portion of the medical instrument based on the sensor signals.

28 Claims, 17 Drawing Sheets

(56) References Cited

U.S. PATENT DOCUMENTS

| | | | |
|---|---|---|---|
| 6,173,715 B1 | 1/2001 | Sinanan et al. | |
| 6,216,028 B1 | 4/2001 | Haynor et al. | |
| 6,263,230 B1 | 7/2001 | Haynor et al. | |
| 6,292,680 B1 | 9/2001 | Somogyi et al. | |
| 7,158,754 B2 | 1/2007 | Anderson | |
| 7,976,518 B2 | 7/2011 | Shaughnessy et al. | |
| 8,197,494 B2 | 6/2012 | Jaggi et al. | |
| 8,265,732 B2 | 9/2012 | Besz et al. | |
| 8,478,382 B2* | 7/2013 | Burnside | A61B 5/06 600/424 |
| 8,606,347 B2 | 12/2013 | Besz et al. | |
| 8,644,907 B2* | 2/2014 | Hartmann | A61B 17/1615 600/424 |
| 8,781,555 B2* | 7/2014 | Burnside | A61B 8/0833 600/424 |
| 8,934,960 B2 | 1/2015 | Besz et al. | |
| 9,028,441 B2 | 5/2015 | Kuhn | |
| 9,131,956 B2 | 9/2015 | Shaughnessy et al. | |
| 9,579,488 B2 | 2/2017 | Shaughnessy et al. | |
| 9,585,599 B2 | 3/2017 | Besz et al. | |
| 9,687,174 B2 | 6/2017 | Jaggi et al. | |
| 2002/0165448 A1* | 11/2002 | Ben-Haim | A61N 1/36564 600/424 |
| 2003/0006759 A1 | 1/2003 | Govari | |
| 2004/0087877 A1 | 5/2004 | Besz et al. | |
| 2006/0211914 A1* | 9/2006 | Hassler, Jr. | A61F 5/0003 600/37 |
| 2008/0004663 A1 | 1/2008 | Jorgenson | |
| 2009/0171190 A1 | 7/2009 | Uchiyama et al. | |
| 2012/0130228 A1 | 5/2012 | Zellers et al. | |
| 2012/0130229 A1 | 5/2012 | Zellers et al. | |
| 2014/0051983 A1* | 2/2014 | Schroeder | A61B 34/20 600/424 |
| 2014/0196723 A1 | 7/2014 | Kirkpatrick et al. | |
| 2015/0238388 A1 | 8/2015 | Kuhn | |
| 2016/0067148 A1 | 3/2016 | Nordquist et al. | |
| 2017/0128701 A1 | 5/2017 | Shaughnessy et al. | |
| 2017/0143235 A1 | 5/2017 | Besz et al. | |

OTHER PUBLICATIONS

U.S. Appl. No. 15/820,001, filed Nov. 21, 2017, Accuracy Testing of Electromagnetic Device Tracking.

U.S. Appl. No. 15/911,006, filed Mar. 2, 2018, Flexible Circuit Bearing a Trackable Low-Frequency Electromagnetic Coil.

U.S. Appl. No. 16/071,891, filed Jul. 20, 2018, Low-Frequency Electromagnetic Tracking.

"Amphenol® RF Frequency Range Chart," URL=https://web.archive.org/web/20151109154937/http://www.amphenolrf.com/frequency-range-chart/, download date Mar. 15, 2017.

International Search Report, dated Apr. 7, 2017, for International Application No. PCT/US2017/014395, 2 pages.

Sacolick et al., "Electromagnetically tracked placement of a peripherally inserted central catheter," *SPIE Medical Imaging Proceedings*, 2004, 5 pages.

* cited by examiner

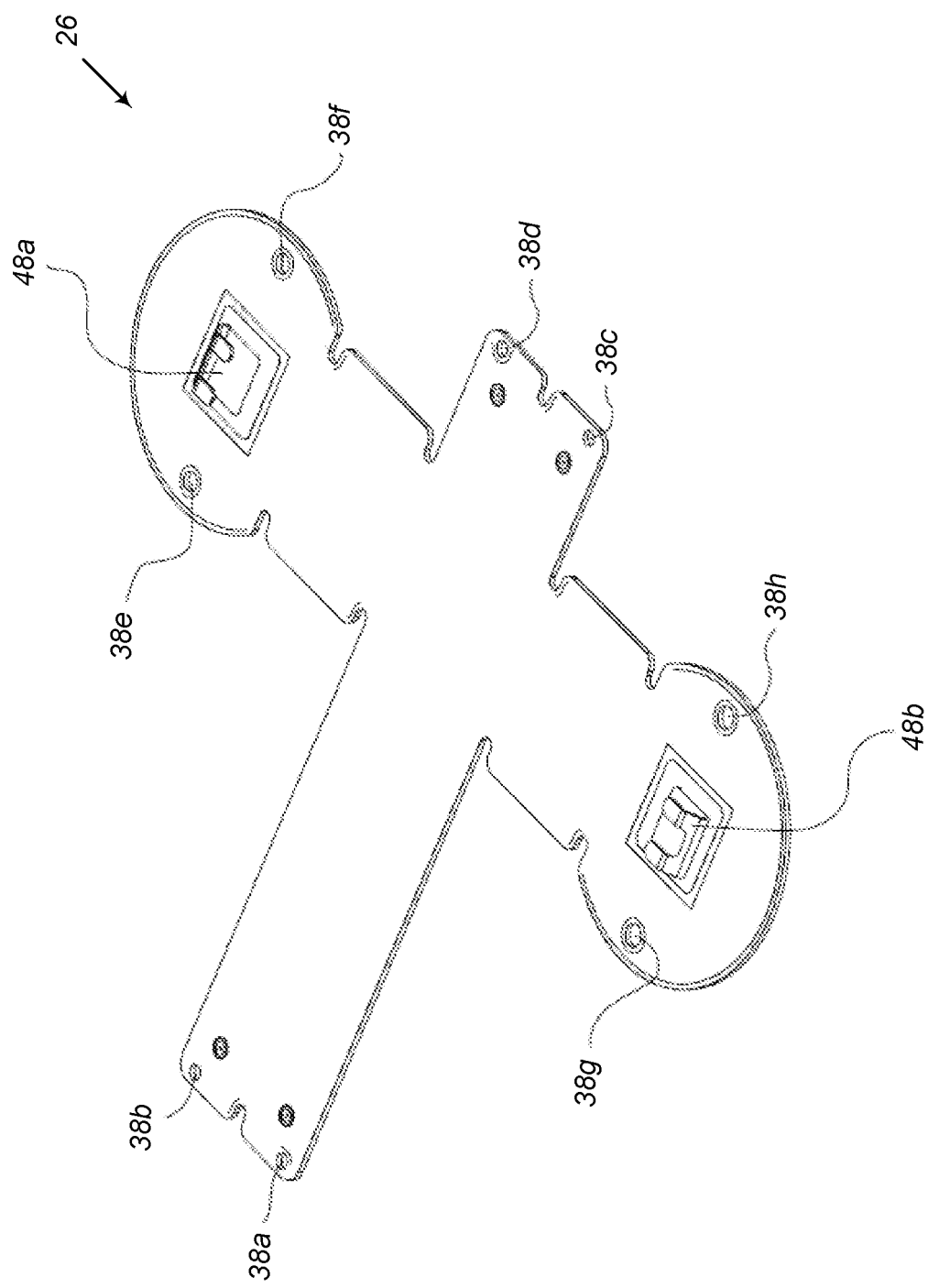

WIRELESS ELECTROMAGNETIC NAVIGATIONAL ELEMENT

TECHNICAL FIELD

The present disclosure generally relates to tracking a medical instrument's position within a body using an electromagnet structure. More particularly, but not exclusively, the present disclosure relates to an electromagnetic navigational element arranged as a pass-through medical device.

BACKGROUND

Description of the Related Art

In many medical procedures, a medical practitioner accesses an internal cavity of a patient using a medical instrument. In some cases, the medical practitioner accesses the internal cavity for diagnostic purposes. In other cases, the practitioner accesses the cavity to provide treatment. In still other cases, different therapy is provided.

Due to the sensitivity of internal tissues of a patient's body, incorrectly positioning the medical instrument within the body can cause great harm. Accordingly, it is beneficial to be able to precisely track the position of the medical instrument within the patient's body. However, accurately tracking the position of the medical instrument within the body can be quite difficult.

It is known that the medical instrument may be tracked as it travels or remains stationary within the patient's body. For example, U.S. Pat. No. 5,425,382 to Golden et al. is entitled, APPARATUS AND METHOD FOR LOCATING A MEDICAL TUBE IN THE BODY OF A PATIENT. The patent describes an apparatus and method for locating a medical tube within the body of a patient. The medical tube is located by a detection apparatus, which senses the static magnetic field strength gradient generated by a magnet associated with the medical tube. The detection apparatus indicates the value of the field strength gradient to the medical practitioner. To use the device, the detection apparatus is moved about the body of the patient until the greatest gradient magnitude is indicated. The detection apparatus distinguishes the field strength of the magnet associated with the medical tube from the earth's field strength by sensing the magnet's field strength at two different distances from the magnet. U.S. Pat. No. 5,425,382 to Golden et al. is incorporated herein by reference to the fullest extent allowed by law.

Other examples are also provided. U.S. Pat. No. 5,622,169 to Golden et al. is entitled, APPARATUS AND METHOD FOR LOCATING A MEDICAL TUBE IN THE BODY OF A PATIENT. The patent describes a method of detecting the location of a magnet associated with a medical tube within the body of a patient. A first static magnetic field strength is sensed at a first distance from the magnet, and a second static magnetic field strength is sensed at a second distance from the magnet. The second distance is greater than the first distance. A first sensor signal is provided as a vector, which is a function of the first static magnetic field strength, and a second sensor signal is provided as a vector, which is a function of the second static magnetic field strength. The difference between the first static magnetic field strength and the second static magnetic field strength is provided as a differential signal vector value. The location of the medical tube can be determined by varying the first and second distances until the greatest value for the differential signal is indicated. U.S. Pat. No. 5,622,169 to Golden et al. is incorporated herein by reference to the fullest extent allowed by law.

U.S. Pat. No. 5,775,322 to Silverstein et al. is entitled, TRACHEAL TUBE AND METHODS RELATED THERETO. The patent describes a tracheal tube for insertion into the trachea of a patient. The tracheal tube includes a tube portion having a distal end, and a signal source such as a permanent magnet associated with the tube portion at a predefined distance from its distal end. The tracheal tube is inserted into the trachea of the patient such that the signal source is immediately posterior to the patient's cricothyroid ligament. Methods related to confirming proper placement of the tracheal tube by detecting the signal source immediately posterior to the patient's cricothyroid ligament are also disclosed. U.S. Pat. No. 5,775,322 to Silverstein et al. is incorporated herein by reference to the fullest extent allowed by law.

U.S. Pat. No. 5,879,297 to Haynor et al. is entitled, SYSTEM AND METHOD TO DETERMINE THE LOCATION AND ORIENTATION OF AN INDWELLING MEDICAL DEVICE. The patent describes a device to detect the location of a magnet coupled to an indwelling medical device within a patient. The device uses three or more sets of magnetic sensors each having sensor elements arranged in a known fashion. Each sensor element senses the magnetic field strength generated by the magnet, and each sensor element provides data indicative of the direction of the magnet in a three-dimensional space. The device uses fundamental equations for electricity and magnetism that relate measured magnetic field strength and magnetic field gradient to the location and strength of a magnetic dipole. The device uses an iterative process to determine the actual location and orientation of the magnet. An initial estimate of the location and orientation of the magnet results in the generation of predicted magnetic field values. The predicted magnetic field values are compared with the actual measured values provided by the magnetic sensors. Based on the difference between the predicted values and the measured values, the device estimates a new location of the magnet and calculates new predicted magnetic field strength values. This iteration process continues until the predicted values match the measured values within a desired degree of tolerance. At that point, the estimated location matches the actual location within a predetermined degree of tolerance. A two-dimensional display provides an indication of the location of the magnet with respect to the housing of the detector. A depth indicator portion of the display can be used to provide a relative or absolute indication of the depth of the magnet within the patient. U.S. Pat. No. 5,879,297 to Haynor et al. is incorporated herein by reference to the fullest extent allowed by law.

U.S. Pat. No. 5,902,238 to Golden et al. is entitled, MEDICAL TUBE AND APPARATUS FOR LOCATING THE SAME IN THE BODY OF A PATIENT. The patent describes a medical tube, an apparatus, and a method for locating the medical tube within the body of a patient. The medical tube has a permanent magnet associated therewith, which is capable of being located by a detection apparatus that senses the static magnetic field strength gradient generated by the permanent magnet. The detection apparatus indicates the value of the gradient to the user. In one embodiment, the magnet is associated with the distal end of the medical tube in a fixed orientation with a magnetic dipole pointing to the proximal end and parallel to a longitudinal axis of the medical tube. In this way, the polarity of the magnet's static magnetic field, as sensed by the detection apparatus, indicates the orientation of the distal end of the medical tube within the body of a patient. U.S. Pat. No. 5,902,238 to Golden et al. is incorporated herein by reference to the fullest extent allowed by law.

U.S. Pat. No. 6,129,668 to Haynor et al. is entitled, SYSTEM AND METHOD TO DETERMINE THE LOCATION AND ORIENTATION OF AN INDWELLING MEDICAL DEVICE. The patent describes a system to detect the position of a magnet associated with an indwelling medical device from a measurement location on the surface of a patient. The system includes a housing and first, second, and third magnetic sensors supported by the housing. Each of the magnetic sensors includes sensor elements to detect magnetic field strength in three orthogonal directions. The first, second, and third magnetic sensors generate first, second, and third sets of signals, respectively, as a function of static magnetic field strength and direction due to the magnet. A processor calculates an estimated position of the magnet in a three-dimensional space and calculates a predicted magnetic field strength for the first, second and third sensors based on the estimated position. The processor also calculates an actual magnetic field strength using the first, second, and third sets of signals and generates an error function based on a difference between the predicted magnetic field strength and the actual magnetic field strength. A display provides a visual display of data related to the position of the magnet in the three-dimensional space using the error function. U.S. Pat. No. 6,129,668 to Haynor et al. is incorporated herein by reference to the fullest extent allowed by law.

U.S. Pat. No. 6,173,715 to Sinanan et al. is entitled, MAGNETIC ANATOMICAL MARKER AND METHOD OF USE. The patent describes an anatomical marker that uses a permanent magnet to indicate a selected location within a patient. The magnet is enclosed within a non-degradable envelope and coupled to a retention member that is preferably manufactured from a biodegradable material, such as a polyglucuronic acid based material. The retention member may include one or more barbs to retain the anatomical marker in the selected location. An insertion tool, usable with an endoscope, can insert the anatomical marker. A retention magnet is fixedly attached to the insertion tool and holds the anatomical marker in place due to the attractive magnetic forces between the retention magnet and the marker magnet in the non-biodegradable envelope. When the anatomical marker is securely fastened at the selected location in the patient, the forces exerted by the patient's body on the retention member exceed the attractive magnetic forces between the retention magnet and the magnet in the envelope, thus causing the anatomical marker to be released from the insertion tool. The location of the magnet may be subsequently detected using a magnetic detector system. U.S. Pat. No. 6,173,715 to Sinanan et al. is incorporated herein by reference to the fullest extent allowed by law.

U.S. Pat. No. 6,216,028 to Haynor et al. is entitled, METHOD TO DETERMINE THE LOCATION AND ORIENTATION OF AN INDWELLING MEDICAL DEVICE. The patent describes a method to detect a position of a magnet associated with an indwelling medical device from a measurement location on the surface of a patient and in the presence of a magnetic field of the Earth. In the method, first, second, and third magnetic sensors having a known spatial relationship with respect to each other are positioned at the measurement location. At the first sensor positioned at a first distance from the magnet, a first set of electrical signals are generated as a function of a first magnetic field strength and direction due to the magnet; at the second sensor positioned at a second distance from the magnet, a second set of electrical signals are generated as a function of a second magnetic field strength and direction due to the magnet; and at the third sensor positioned at a third distance from the magnet, a third set of electrical signals are generated as a function of a third magnetic field strength and direction due to the magnet. An estimated position of the magnet in a three-dimensional space is calculated, and a predicted magnetic field strength for the first, second and third sensors based on the estimated position is also calculated. The effects of the Earth's magnetic field are canceled by subtracting a first selected one of the first, second, and third sets of electrical signals from a second selected one of the first, second, and third sets of electrical signals different from the first selected one of the first, second, and third sets of electrical signals to thereby generate a measured magnetic field strength using the first, second, and third sets of electrical signals. An error function is generated based on a difference between the predicted magnetic field strength and the measured magnetic field strength, and the three-dimensional position of the indwelling device is indicated by providing a visual display of the three-dimensional position of the associated magnet using the error function. U.S. Pat. No. 6,216,028 to Haynor et al. is incorporated herein by reference to the fullest extent allowed by law.

U.S. Pat. No. 6,263,230 to Haynor et al. is entitled, SYSTEM AND METHOD TO DETERMINE THE LOCATION AND ORIENTATION OF AN INDWELLING MEDICAL DEVICE. The patent describes a system to detect a position of a plurality of magnets within a patient from a measurement location outside the patient. The system includes a housing and a plurality of magnetic sensors supported by the housing. Each of the plurality of sensors is oriented in a known direction and generates a set of signals as a function of static magnetic field strength and direction due to the plurality of magnets within the patient. A processor calculates an estimated position of each of the plurality of magnets in a three-dimensional space and calculates values of a predicted magnetic field strength for at least a portion of the plurality of sensors based on the estimated positions of each of the plurality of magnets. The processor also calculates values of an actual magnetic field strength using the set of signals and determines values of the location of each of the plurality of magnets based on the difference between the values of the predicted magnetic field strength and the values of the actual magnetic field strength. A display provides a visual display of the position of each of the plurality of magnets in the three-dimensional space. U.S. Pat. No. 6,263,230 to Haynor et al. is incorporated herein by reference to the fullest extent allowed by law.

U.S. Pat. No. 6,292,680 to Somogyi et al. is entitled, NON-INVASIVE SENSING OF A PHYSICAL PARAMETER. The patent describes a method and device for non-invasively sensing a physical parameter within the body of a patient by employing a magnetically-based sensing device and a monitoring device. The magnetically-based sensing device has a first magnet and a second magnet, which generate a combined magnet field. The first and second magnets are positioned such that a change in a physical parameter causes a change in the combined magnet field, and the change is monitored by the monitoring device. U.S. Pat. No. 6,292,680 to Somogyi et al. is incorporated herein by reference to the fullest extent allowed by law.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY

A system may be summarized as including: a medical instrument, the medical instrument including: a needle-position-tracking element having a through-port body that is arranged for fluid communication between a syringe and a needle, a circuit assembly proximal to the through-port body, and a housing that contains the through-port body and the circuit assembly, the circuit assembly including: an electromagnet structure having a length substantially parallel to a length of the needle when the needle is arranged in fluid communication with the through-port body, the electromagnet structure having a core and a conductive coil wound around the core; and ancillary circuitry electrically coupled to the conductive coil, the ancillary circuitry configured to controllably drive an excitation signal through the conductive coil to thereby generate a magnetic field about the electromagnet structure.

The medical instrument may further include: a needle having an internal bore and the length, the needle structured for at least partial insertion into a body of a patient, the needle structured to transfer a substance to or from the body of the patient; and a syringe having a first chamber to contain the substance. The system may further include: a sensor device configured to sense the magnetic field generated when the excitation signal is driven through the conductive coil and further configured to generate a sensor signal representative of at least one portion of the sensed magnetic field; and a control circuit configured to calculate information corresponding to a position of the needle within the body of the patient based on the sensor signal. The control circuit configured to calculate the information corresponding to the position of the needle within the body of the patient may be further configured to: determine a position of the electromagnet structure from the sensor signal; and determine the position of the needle based on the position of the electromagnet structure and further based on a known positional relationship of the needle relative to the electromagnet structure. The through-port body may include a carrier body and a through-port chamber, the carrier body having at least one mounting hole for securely aligning the through-port body to the housing, wherein the through-port chamber is structured to permit a transfer of a liquid through the needle-position-tracking element between the syringe and the needle. The through-port chamber may be adjacent and substantially parallel to the electromagnet structure. The system may further include: a first female luer locking port integrated with the needle; a first male luer locking hub integrated with the syringe; a second male luer locking hub integrated with the through-port body and connected to the first female luer locking port of the needle; and a second female luer locking port integrated with the through-port body and connected to the first male luer locking port of the syringe. The circuit assembly may include a flexible portion arranged around the through-port body. The substance may be a liquid. The substance may be a non-liquid. The system may further include: a plurality of mounting posts integrated with the through-port body; and a plurality of mounting holes integrated in the circuit assembly, the plurality of mounting holes engaging the plurality of mounting posts to secure the circuit assembly to the through-port body. The circuit assembly may further include: a second electromagnet structure having a second core and a second conductive coil wound around the second core, the second electromagnet structure arranged substantially parallel to the electromagnet structure; and second ancillary circuitry electrically coupled to the second conductive coil, the second ancillary circuitry configured to controllably drive a second excitation signal through the second conductive coil to thereby generate a second magnetic field about the second electromagnet structure. The through-port body may contain at least one battery arranged to supply power to the ancillary circuitry.

A medical device may be summarized as including: a through-port body having a first locking structure at a first end, a second locking structure at a second end opposite of the first end, and a through-port chamber having a length that is in liquid communication between the first locking structure and the second locking structure; a circuit assembly proximal to the through-port body, the circuit assembly including: an electromagnet structure formed with a core and a conductive coil wound around the core; and ancillary circuitry electrically coupled to the conductive coil, the ancillary circuitry configured to drive an excitation signal through the conductive coil to thereby generate a magnetic field about the electromagnet structure; and a housing that contains the through-port body and the circuit assembly.

The first locking structure may be a luer locking hub and wherein the second locking structure may be a luer locking port. The first locking structure may be a male luer locking hub and wherein the second locking structure may be a female luer locking port. The first locking structure of the through-port body may be arranged for connection to a needle having a first cooperative locking structure, and wherein the second locking structure of the through-port body may be arranged for connection to a syringe having a second cooperative locking structure. The first and second locking structures and the first and second cooperative locking structures may be arranged according to a luer locking structure. The electromagnet structure may have a length that is parallel to the needle when the through-port body is connected to the needle having the first cooperative locking structure. The electromagnet structure may have a length that is parallel to the through-port chamber. The circuit assembly may include: a first portion having a first battery contact that is electrically coupled to the ancillary circuitry; a second portion having a second battery contact that is electrically coupled to the ancillary circuitry; and a flexible third portion disposed between the first and second portions to at least partially wrap the circuit assembly around the through-port chamber and thereby arrange the first portion substantially parallel to the second portion and further arrange the first battery contact opposite to the second battery contact. The through-port body may include: a carrier body having at least one mounting hole arranged to align and secure the through-port body to the housing. The medical device may include: a plurality of mounting posts integrated in the through-port body; and a plurality of mounting holes integrated in the circuit assembly, wherein the plurality of mounting holes are arranged to engage the plurality of mounting posts to secure the circuit assembly to the through-port body. The through-port body may include: a battery well to house at least one battery.

A method to make a medical device may be summarized as including: providing an electromagnet structure secured to a partially flexible circuit structure, the electromagnet structure having a wire-like conductor wound into a coil around a core; securing battery contacts to the flexible circuit structure; electrically connecting ancillary circuitry to the coil and to the battery contacts; forming a through-port body having a through-port chamber and a carrier body having a battery well; wrapping the flexible circuit structure around the through-port chamber such that the battery contacts are aligned opposite one another about the battery well; and containing the wrapped flexible circuit structure and the through-port body in a housing.

The method may further include: attaching a needle to a first end of the through-port chamber; and attaching a syringe to a second end of the through-port chamber.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. The shapes of various elements and angles are not necessarily drawn to scale either, and some of these elements are enlarged and positioned to improve drawing legibility. One or more embodiments are described hereinafter with reference to the accompanying drawings in which:

FIGS. 3A-3D are illustrations of a circuit assembly of a needle-position-tracking element, according to one embodiment;

DETAILED DESCRIPTION

Figure 1:
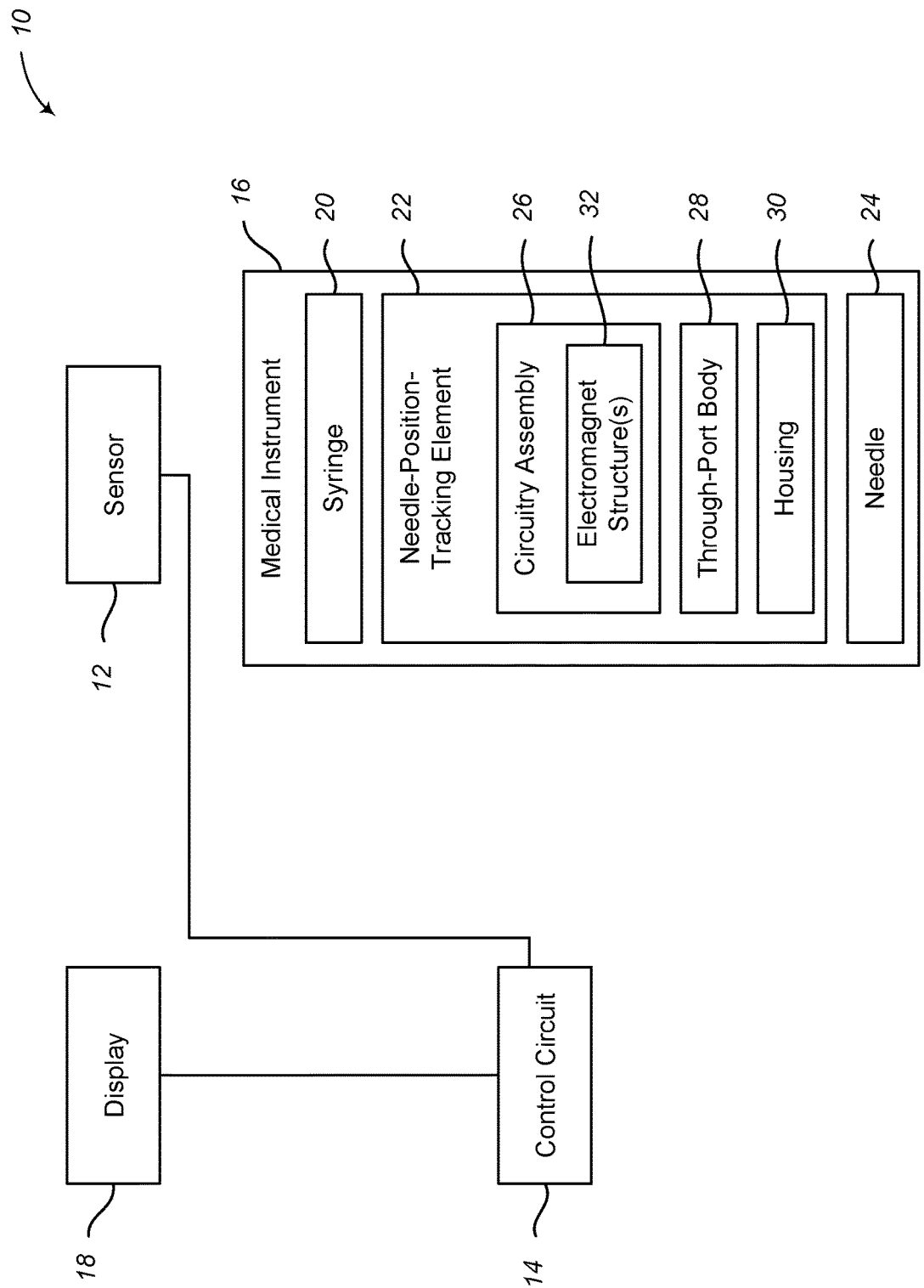
FIG. 1 is a block diagram of a system for detecting the position of a portion of a medical instrument within a body of a patient, according to one embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. Also in these instances, well-known structures may be omitted or shown and described in reduced detail to avoid unnecessarily obscuring descriptions of the embodiments.

Prior to setting forth the embodiments, however, it may be helpful to an understanding thereof to first set forth definitions of certain terms that are used hereinafter.

"Medical instrument" refers to a device, instrument, apparatus, constructed element or composition, machine, implement, or similar or related article that can be utilized to diagnose, prevent, treat or manage a disease or other condition(s). For example, medical instruments are used on patients in surgery, preventive care, diagnosis of disease or other condition, treatment, and a wide range of other physiological processes. A medical instrument is a device used in a procedure on the body of a subject (e.g., a patient). Medical instruments include various different types of needle and syringe devices that are used to insert or extract liquid or other material to or from the body of the patient as the case may be. In many embodiments the medical instruments discussed herein are sterile and subject to regulatory requirements relating to their sale and use.

An "electromagnet structure," or interchangeably an "electromagnetic structure," is a structure that includes one or more electromagnets. The electromagnet structure(s) is(are) aligned in a determined orientation relative to the medical instrument. Each electromagnet structure is created having a wire-like conductor wound into a coil, and a core structure located fully or partially within the center of the coil. For example, an electromagnet structure may be formed by winding a copper-based wire around a ferrous rod core structure.

The "wire-like conductor" of a coil in an electromagnet structure may be a wire, a trace manufactured with any type of manufacturing process (e.g., a semiconductor process, a printed circuit process, and the like), or some other such structure. The wire-like conductor may have a cross-reference shape that is circumferential, substantially circular, substantially square, octagonal, hexagonal, or having some other cross-section. The wire-like conductor may be arranged in a coil structure by winding the wire-like conductor around the core structure. Alternatively, the wire-like conductor may be arranged in a coil by another process and the core structure may be later placed centrally in the inner void of the coil. The wire-like conductor may be formed from copper, a copper alloy, gold, tin, or some other electrically conductive material.

"Contain" in all of its grammatical forms refers to one structure being integrated or otherwise located inside another structure. Contain includes encase, enclose, encapsulate, surround, envelop, confine, and other like terms. When a first structure contains a second structure, the containment may be total or partial. For example, a housing may contain an electronic circuit. The housing may have holes, slots, open sides, or other features that allow some or all of the electronic circuit to be seen without opening or otherwise manipulating the housing. As another example, an insulating jacket may contain a wire, a lumen may contain an electromagnet structure, and a conductive coil may contain a ferrous-based core structure.

In many medical situations, it is desirable to penetrate the solid or semi-solid biological matter of a patient's body and guide a portion of a medical instrument to a precise location. For example, one common medical practice involves inserting a needle into a vein or artery of a patient's body to supply a drug or other liquid into the bloodstream of the patient. As described herein, the medical instrument includes a needle, a syringe, and a needle-position-tracking element in fluid communication disposed between the syringe and the needle. When a portion of the needle penetrates and passes into the patient's body, it may be desirable to know the precise location, angle, or depth of the needle in the patient's body. An electromagnet structure contained in the needle-position-tracking element is aligned relative to the needle such that when it is driven with a low-frequency excitation signal, the electromagnet structure will be trackable to a precise location relative to the patient's body and the needle, which is used to approximate, with a high degree of accuracy, the position of the needle within the body of the patient.

Briefly, the system also includes a magnetic field sensing device (e.g., a sensor or a sensor device), control circuitry, and a presentation system. The field sensing device is operated by a medical practitioner proximal to the body of the patient, which senses and tracks the position of the electromagnetic structure. Generally, the medical practitioner will attempt to place the magnetic field sensing device adjacent to the portion of the patient's body where the medical instrument is being used.

Embodiments of the presentation system are used to present information representing the position and orientation of a needle of the medical instrument when the needle is advanced, for example, in the patient's body. The presentation system includes one or more of a video display, an audio input/output system, a tactile feedback system, or some other presentation mechanism. The presentation system may further include one or more user input interfaces for keyboards, mice, touch screens, buttons, dials, and other like controls.

The control circuitry provides input information to the magnetic field sensing device and receives output information from the magnetic field sensing device, including magnetic field information. Magnetic field information is generated when a low-frequency excitation signal is applied to the electromagnet structure in the needle-position-tracking element of the medical instrument. The magnetic field sensing device captures the magnetic field information and provides it to the control circuitry. The control circuitry uses the magnetic field information and other positioning information (e.g., the position of the magnetic field sensing device relative to the patient) to track the position of the electromagnet structure of the medical instrument. The known position and orientation of the needle relative to the electromagnet structure is used to track the needle as it is advanced into and through the body of the patient. The control circuitry provides tracking information to the presentation system for display to the medical practitioner.

The present invention may be understood more readily by reference to the following detailed description of the preferred embodiments of the invention. It is to be understood that the terminology used herein is for the purpose of describing specific embodiments only and is not intended to be limiting. It is further to be understood that unless specifically defined herein, the terminology used herein is to be given its traditional meaning as known in the relevant art.

FIG. 1 is a block diagram of a system 10 for detecting the position of a portion of a medical instrument 16 within the body of a patient, according to one embodiment. The system 10 includes a medical instrument 16, a sensor 12, a presentation system 18, and a control circuit 14. The control circuit 14 is coupled to the sensor 12 and the presentation system 18. It is recognized that the systems, devices, and methods described in the present disclosure may also track a portion of the medical instrument in general, i.e., before the portion of the medical instrument is advanced into and within the body of the patient, while the portion of the medical instrument is in the body, as the portion of the medical instrument is withdrawn from the body, and after the portion of the medical instrument has been withdrawn from the body. For brevity, however, and to particularly focus on the ideas discussed in the present disclosure without unnecessarily obscuring them, "tracking" is discussed as occurring when the portion of the medical instrument 16 is "within the body of a patient."

The medical instrument 16 is a medical device configured such that at least a portion of the medical device is to be introduced into the body of a patient in conjunction with a medical procedure. The patient may be a human patient or a non-human patient. The medical instrument 16 includes a syringe 20, a needle-position-tracking element 22, and a needle 24. The needle-position-tracking element 22 is disposed between the syringe 20 and the needle 24 and is configured to allow liquid to flow between the syringe 20 and the needle 24 via the needle-position-tracking element 22.

Figure 2:
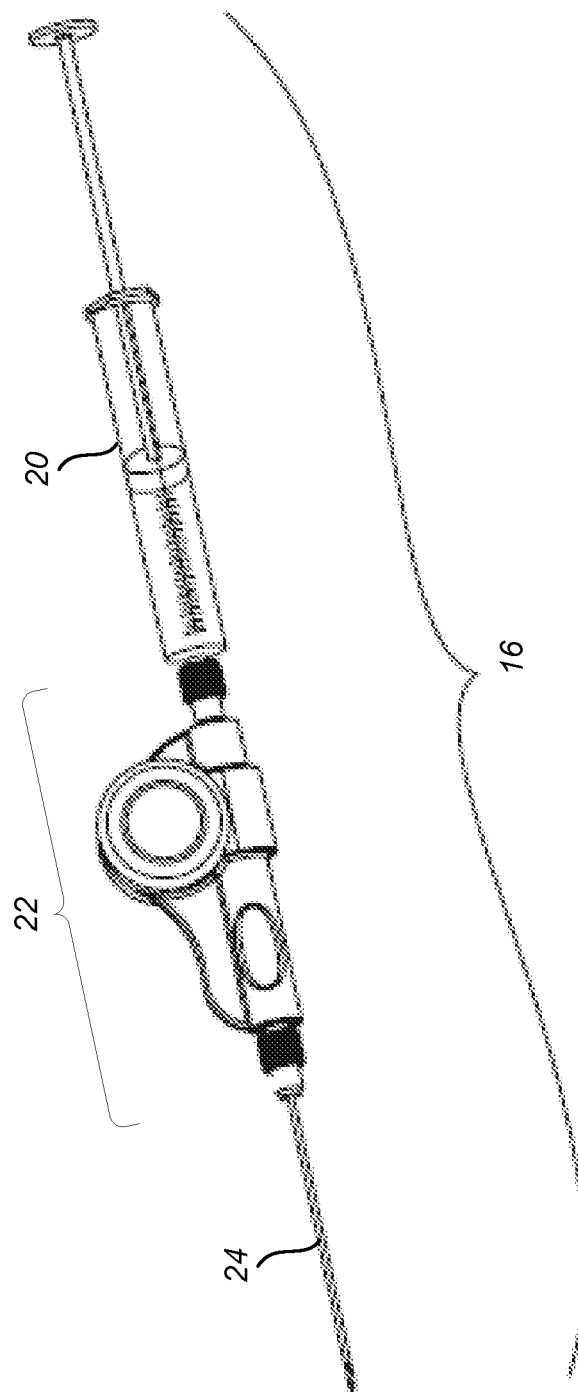
FIG. 2 is an illustration of a medical instrument having a syringe, a needle, and a needle-position-tracking element, according to one embodiment.

The syringe 20 is configured to contain and supply a liquid to, or extract a liquid from, the patient's body via the needle 24. As the term is used herein, the liquid may be a viscous liquid, a gel, or some other material having liquid-like properties that permit travel of the material through a lumen of a medical device. In various embodiments, the syringe 20 includes a plunger (e.g., as illustrated in FIG. 2) that is configured to influence the flow of liquid to be expelled from or accepted into the syringe 20. In other embodiments, the syringe 20 may not include a plunger, and the flow of liquid may be achieved via pre-existing pressure differences between the syringe 20 and the patient's body (e.g., a blood-draw test tube).

It is recognized that the medical devices and methods described in the present disclosure, which are interchangeably referred to herein as a needle, may also pass other materials besides liquids. For example, the needle may pass an implant such as a therapy-dispensing plastic or medical marker, a biological sample (e.g., biological tissue or other biological material passed into the patient for therapy or out from the patient for study), or some other substance that is not a liquid or not traditionally described as a liquid. For brevity, however, and to particularly focus on the ideas discussed in the present disclosure without unnecessarily obscuring them, the term, "liquid," is broadly understood to also include these non-liquid substances unless the context requires otherwise.

The needle 24 is configured to be inserted into a patient's body and to transfer liquid into or out of the patient's body via a central bore chamber.

The needle-position-tracking element 22 includes a circuit assembly 26, a through-port body 28, and a housing 30. The through-port body 28 is configured to attach to and allow liquid to pass between the syringe 20 and the needle 24. The housing is configured to contain and protect the circuit assembly 26 and the through-port body 28. As described in more detail herein, the circuit assembly 26 includes at least one electromagnet structure 32 that includes a conductive coil wound about a core (e.g., a ferrous-based core structure).

In many medical procedures, it can be advantageous to accurately track the position of the needle 24 within the body of the patient. For example, if the medical instrument 16 is delivering fluid to a particular part of the patient's body, then it can be advantageous to accurately track the position of the needle 24 to provide confidence that the needle 24 is in the correct position for fluid delivery. In some particularly sensitive medical procedures, knowing the exact position of the needle 24 with substantial certainty can improve the well-being of the patient during a medical procedure.

The needle-position-tracking element 22 (and the electromagnet structures contained therein) enables tracking of the position of the needle 24. When a current is passed through the electromagnet structure 32, a detectable and trackable magnetic field is generated. The magnetic field can enable detection and tracking of the medical instrument 16.

In one embodiment, the circuit assembly 26 includes electrical components to drive the electromagnet structure 32 with a low frequency excitation signal or with a DC signal or a high-frequency excitation signal. The excitation signal causes a current to be passed through the electromagnet structure 32. As the direction and magnitude of the current change, the parameters (i.e., characteristics) of the magnetic field generated by the electromagnet structure 32 also change. The magnetic field generated by the electromagnet structure 32 has particular characteristics based in part on the waveform of the excitation signal. These particular oscillating characteristics can enable the sensor 12 to distinguish the magnetic field from noise, interference, and/or other magnetic fields. In this way, the sensor 12 can track the position of the medical instrument 16 with acceptable accuracy even when the medical instrument 16 is deep within the body of the patient.

In one embodiment, the electromagnet structure 32 is driven with an excitation signal having a frequency less than 10,000 Hz. In one embodiment, the electromagnet structure 32 is driven with an excitation signal having a frequency less than 500 Hz. In one embodiment, the electromagnet structure 32 is driven with an excitation signal having a frequency of about 330 Hz. The selection of a 330 Hz excitation signal may help to avoid AC line related components, which might occur at a multiple of a line frequency. For example, 300 Hz, which is a multiple of both 50 Hz and 60 Hz—two common line frequencies in Europe and the U.S., respectively—may provide strong magnetic returns, but the strong magnetic returns may also have measurable harmonic components associated with the AC line frequency.

The sensor 12 includes one or more magnetic sensors that sense a magnetic field created when an excitation signal is driven through the electromagnet structure 32. The sensor 12 generates data representative of the magnetic field generated by the electromagnet structure 32. The sensor 12 can detect parameters of the magnetic field such as field strength and direction. The sensor 12 generates one or more sensor signals indicative of parameters of the magnetic field. The position of the medical instrument 16, along with orientation, motion, and other location-based information can be determined based on the parameters of the magnetic field generated by the electromagnet structure 32.

The control circuit 14 is a processor or controller that calculates location-based information (e.g., position, orientation, motion, and the like) of the medical instrument 16. The control circuit 14 receives the one or more sensor signals from the sensor 12 and analyzes the one or more sensor signals. The control circuit 14 generates the location-based information, such as the position of the medical instrument 16, based on the one or more sensor signals. In particular, the control circuit 14 determines a position of the electromagnet structure 32 from the sensor signals. The control circuit 14 then determines the location-based information of the needle 24 based on the position of the electromagnet structure 32 and the known position of the needle 24 relative to the electromagnet structure 32.

In one embodiment, the control circuit 14 is separate from the medical instrument 16. In some other embodiments, the control circuit 14 may be integrated into the medical instrument 16. Moreover, embodiments described herein refer to the needle-position-tracking element 22 of the medical instrument 16 as including a power source to drive the excitation signal through the electromagnet structure 32. However, in some other embodiments, the control circuit 14 may remotely drive the excitation signal through the electromagnet structure 32.

In one embodiment, the control circuit 14 executes particular algorithms to identify and track the position of the medical instrument 16, the needle 24 in particular, in three dimensions, and the orientation of medical instrument 16 relative to a reference point, based on the position of the electromagnet structure 32. In these and other cases, tracking the position of the medical instrument 16 includes integrating current and historical position data in order to predict one or more future positions of the medical instrument 16. In some embodiments, the control circuit 14 receives information from other devices (e.g., an ultrasound device) to determine a position of the patient's body and the anatomical structure therein.

In one embodiment, the presentation system 18 displays a visual representation of the position of the needle 24 within the body of the patient. Here, the position of the needle 24 or the position of a portion of the needle (e.g., the distal tip of the needle) may be deduced from the detected position of the electromagnet structure 32 and the known physical relationship between the electromagnet structures 32 and the needle 24. In some embodiments, the presentation system 18 displays a visual representation of the entire medical instrument 16. The visual representation of the position of the needle 24 or the medical instrument 16 enables medical personnel to accurately know the position of the needle 24 within the body of the patient or the position of the medical instrument 16 relative to the body of the patient. This, in turn, can enable the medical personnel to correctly perform medical procedures on the patient.

In one embodiment, the control circuit 14 generates a video signal and outputs the video signal to the presentation system 18. The video signal includes a representation of the position of the needle 24 within the body of the patient. The video signal can also include position data that can be displayed on the presentation system 18. The position data can include text that indicates numerical coordinates representing the position, orientation, and motion of the needle 24 or the medical instrument 16. The presentation system 18 can display both the visual representation of the position of the needle 24 within the body of the patient and the position data indicating the position of the needle 24 within the body of the patient. In some embodiments, the presentation system 18 can also display the visual representation of the position of the entire medical instrument 16 to provide the medical personnel with a visual representation of the position of the medical instrument 16 relative to the patient's body.

The control circuit 14 may include multiple discrete control circuit portions. The control circuit 14 can include one or more microcontrollers, one or more microprocessors, one or more memory devices, one or more voltage sources, one or more current sources, one or more analog-to-digital converters, one or more digital-to-analog converters, and/or one or more wireless transceivers. One or more of these components can collectively make up the control circuit 14.

FIG. 2 is an illustration of a medical instrument 16 having a syringe 20, a needle 24, and a needle-position-tracking element 22, according to one embodiment. Briefly shown in this figure, the needle-position-tracking element 22 is connected the needle 24 and to the syringe 20 such that the needle-position-tracking element 22 is positioned between the needle 24 and the syringe 20. In this way, liquid can flow from the syringe 20 through the needle-position-tracking element 22 and then through the needle 24. Likewise, liquid can flow from the needle 24 through the needle-position-tracking element 22 and into the syringe 20.

Figure 3A:
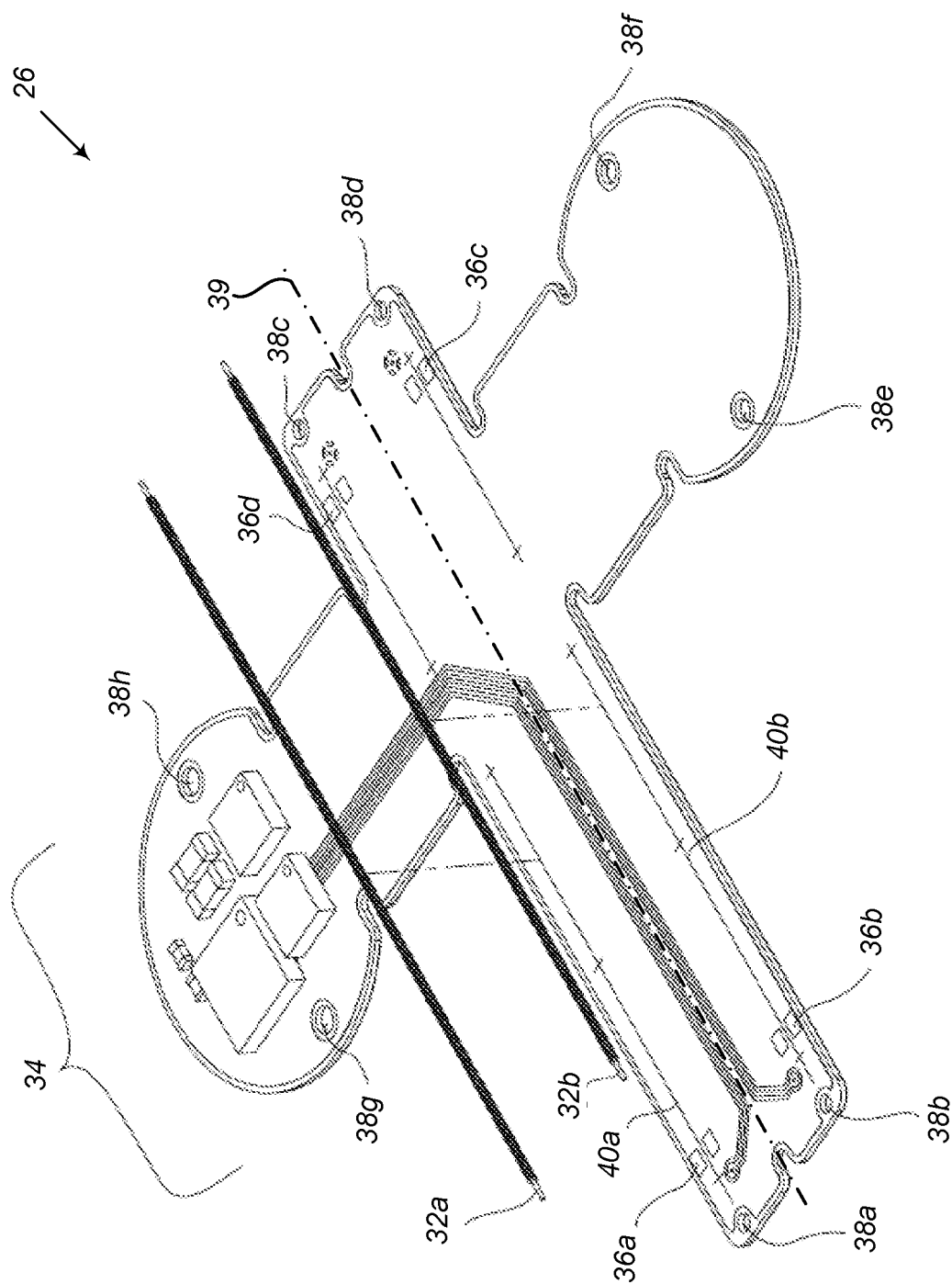
Figure 3C:
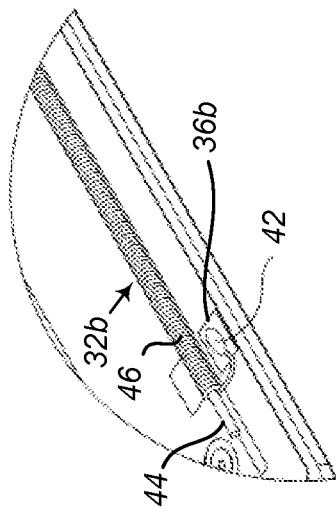
Figure 3B:
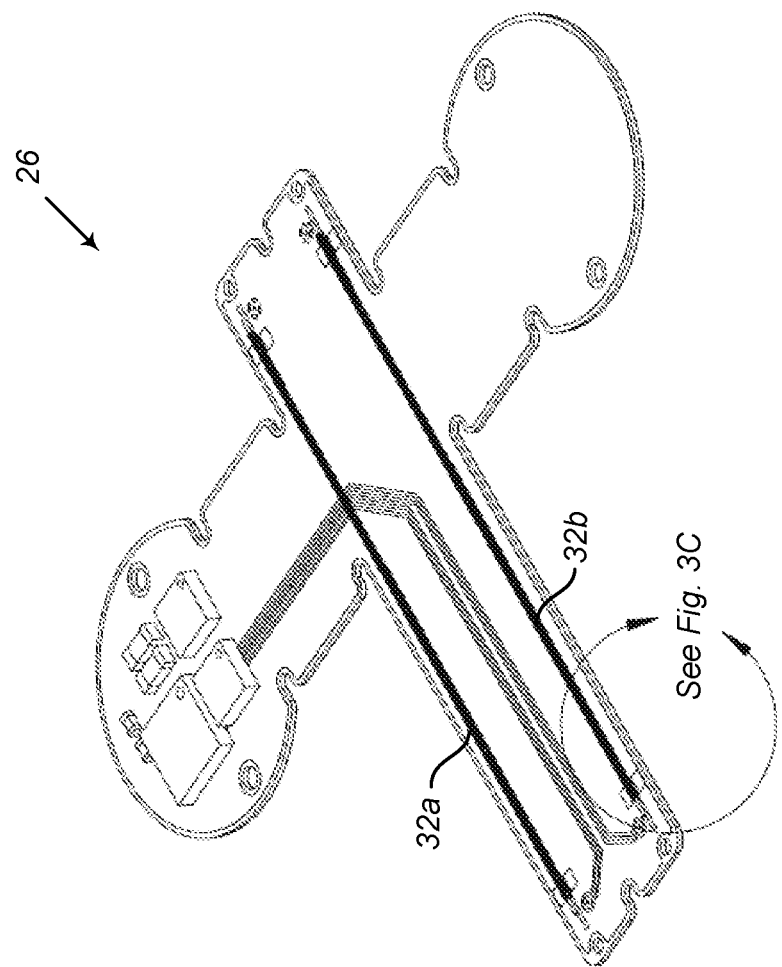

FIGS. 3A-3D illustrate a circuit assembly 26 of a needle-position-tracking element 22 (FIG. 2), according to one embodiment. FIGS. 3A-3C are top perspective illustrations of the circuit assembly 26, with FIG. 3A being a partially exploded view. In general, the circuit assembly 26 is a flexible circuit or a partially flexible circuit. This flexibility enables the circuit assembly 26 to fold about a central axis 39 and around a through-port body 28 (not shown in FIG. 3A) of the needle-position-tracking element 22, as discussed in the present disclosure.

The circuit assembly 26 includes ancillary circuitry 34 and electromagnet structures 32a-32b. The ancillary circuitry 34 includes various electronic components that drive an excitation signal through the electromagnet structures 32a-32b. In the illustrated embodiment, the electromagnet structures 32a-32b are shown in an exploded view of the circuit assembly 26. The positioning of the electromagnet structure 32a is along coil alignment mark 40a, and the positioning of the electromagnet structure 32b is along coil alignment mark 40b. The coil alignment marks 40a-40b are parallel to a central axis 39 of the circuit assembly 26. This positioning of the electromagnet structures 32a-32b is configured such that the electromagnet structures 32a-32b are substantially parallel to the needle 24, as discussed in the present disclosure. Stated another way, the axis of the medical instrument (e.g., the needle) is circumferentially between the electromagnet structures 32a-32b as depicted in FIGS. 5D and 6A-6C.

The circuit assembly 26 includes a plurality of solder pads 36a-36d that are electrically coupled to the ancillary circuitry 34. The solder pads 36a-36d are configured such that one end of a corresponding electromagnet structure 32a-32b can be electrically coupled (e.g., via solder paste) to a corresponding solder pad 36a-36d, which electrically couples the electromagnet structures 32a-32b to the ancillary circuitry 34. For example, a first end of the electromagnet structure 32a is electrically coupled to solder pad 36a, and a second end of the electromagnet structure 32a is electrically coupled to solder pad 36d. Similarly, a first end of the electromagnet structure 32b is electrically coupled to solder pad 36b, and a second end of the electromagnet structure 32b is electrically coupled to solder pad 36c. The electric coupling between the electromagnet structures 32a-32b and the solder pads 36a-36d electrically couples the electromagnet structures 32a-32b to the ancillary circuitry 34, and thus allowing the ancillary circuitry 34 to drive an excitation signal through the electromagnet structures 32a-32b. In some embodiments, the solder pads 36a-36d also provide a support structure for connecting the electromagnet structures 32a-32b to the circuit assembly 26.

In various embodiments, the ancillary circuitry 34 can drive the same excitation signal through both electromagnet structures 32a-32b. In other embodiments, the ancillary circuitry 34 can drive different excitation signals through the electromagnet structures 32a-32b such that the generated magnetic fields are different. In this way, the sensors 12 (shown in FIG. 1) can sense the different magnetic fields, and the control circuit 14 (shown in FIG. 1) can detect the positioning of each separate electromagnet structure 32a-32b, which allows for the control circuit 14 to generate a more accurate three-dimensional position of the medical instrument 16.

The circuit assembly 26 also includes a plurality of mounting holes 38a-38h. The mounting holes 38a-38h are configured such that pins or support bosses can pass through corresponding mounting holes 38a-38h to align the circuit assembly 26 with the through-port body 28 (not shown) of the needle-position-tracking element 22, and optionally the housing 30 (not shown) of the needle-position-tracking element 22, as discussed herein.

In some embodiments, the electromagnet structures 32a-32b include an inductor coil wrapped around a core. FIGS. 3B-3C illustrate the electromagnet structure 32b as including an inductor coil 46 wrapped around a core 44. At each end of the inductor coil 46 is a coil contact 42. The coil contact 42 is electrically coupled, such as by using solder paste, to the solder pad 36b. Although not illustrated, similar structures and electric couplings may also be arranged at the other end of the inductor coil 46 and at both ends of the corresponding inductor coil of the electromagnet structure 32a.

FIG. 3D is a bottom perspective illustration of the circuit assembly 26. As discussed herein, the circuit assembly 26 includes a plurality of mounting holes 38a-38h that are configured such that pins or support bosses can pass through corresponding mounting holes 38a-38h to align, secure, or align and secure the circuit assembly 26 with the through-port body 28 (not shown). The circuit assembly 26 also includes battery contacts 48a-48b. The battery contacts are electrically coupled to the ancillary circuitry 34 to electrically couple one or more batteries (not illustrated) to the ancillary circuitry 34 to provide power. Such power may be used to drive the excitation signal through the electromagnet structures 32a-32b and for other purposes.

Although embodiments described herein illustrate the circuit assembly 26 as having two electromagnet structures 32a-32b, other embodiments may include one or three or more electromagnet structures. Moreover, although the FIGS. 3A-3D illustrate the electromagnet structures 32a-32b as being positioned on a top face (i.e., the same face of the ancillary circuitry 34) of the circuit assembly 26, the electromagnet structures 32a-32b may be positioned on a bottom face (i.e., a face opposite of the ancillary circuitry 34) in other embodiments.

Figure 4A:
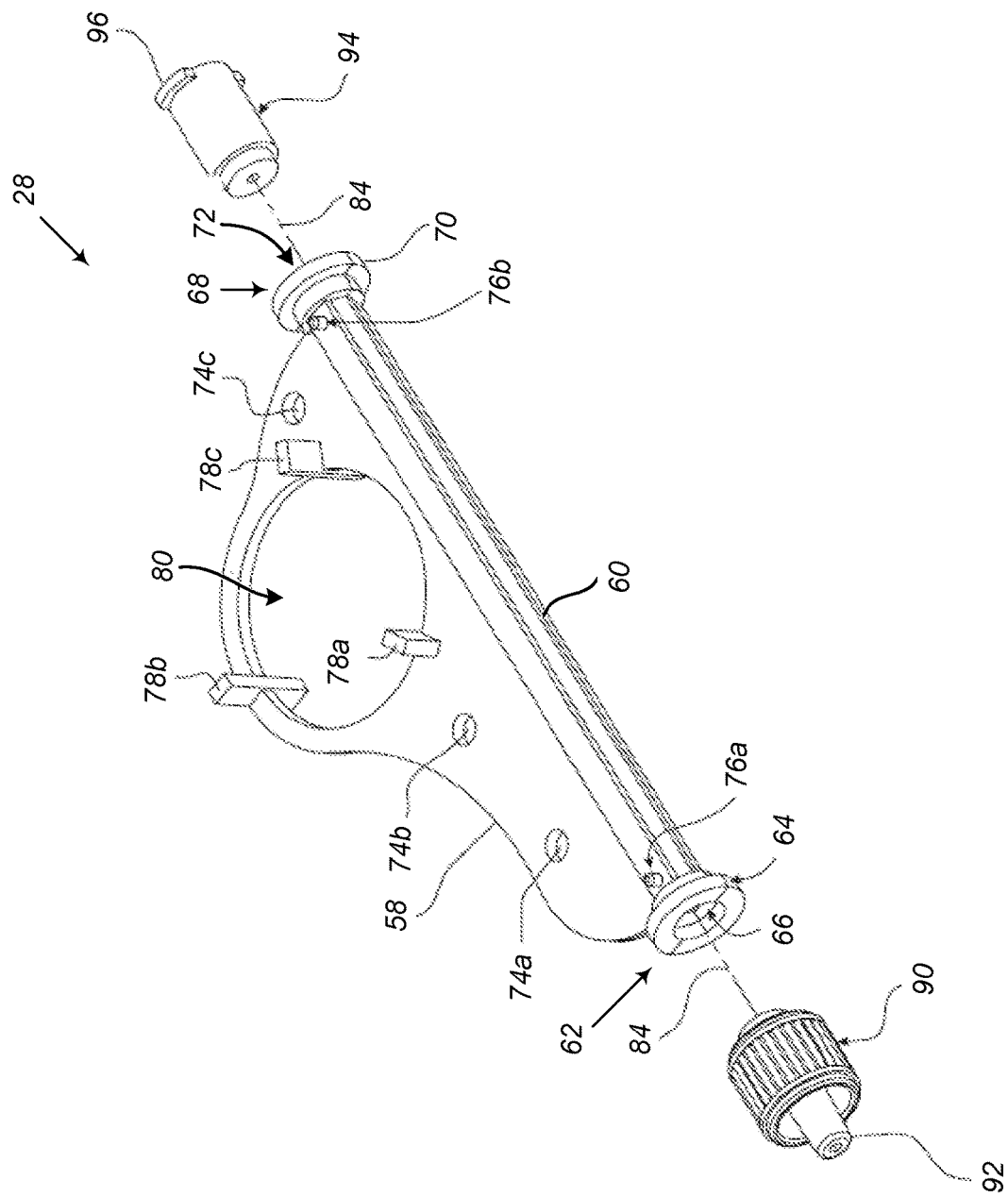
FIGS. 4A-4C are illustrations of a through-port body of the needle-position-tracking element, according to one embodiment.
Figure 4B:
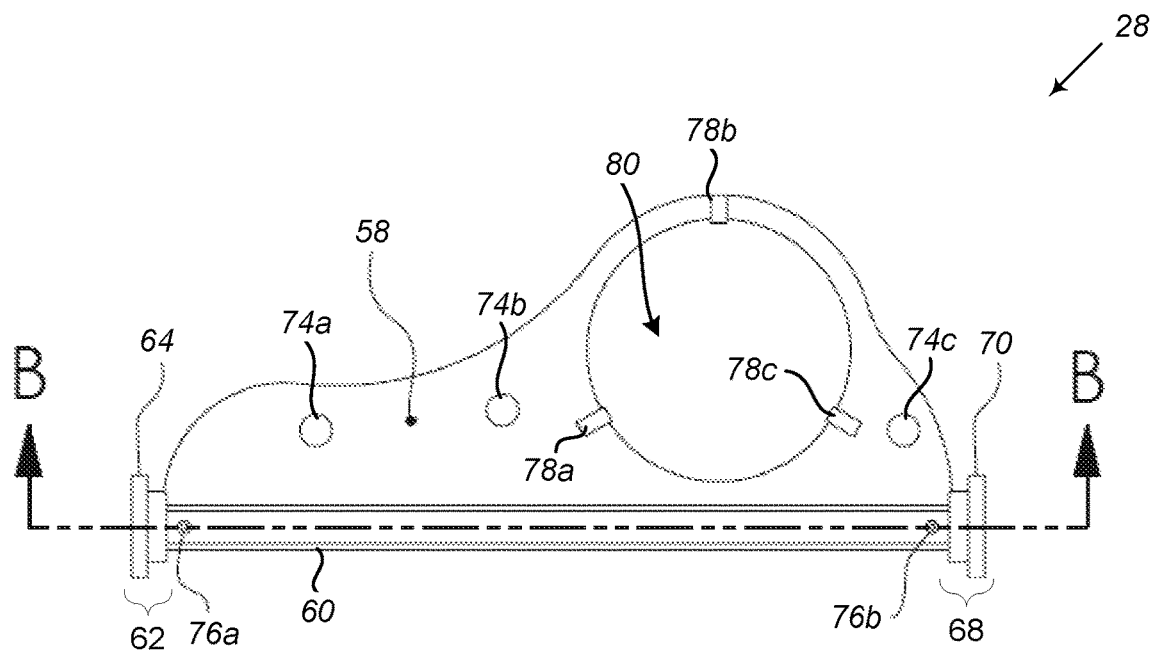
Figure 4C:
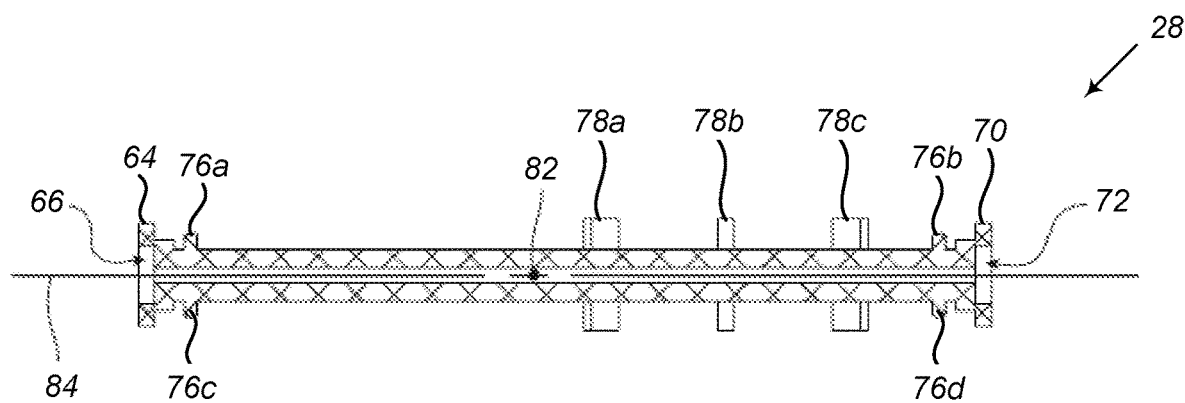

FIGS. 4A-4C are illustrations of the through-port body 28 of the needle-position-tracking element 22 (FIG. 2), according to one embodiment. FIG. 4A is an exploded perspective view of the through-port body 28. The through-port body 28 includes a carrier body 58 and a through-port chamber 60.

The through-port chamber 60 includes a distal hub 62 at one end and a proximal hub 68 at the other end, both of which are arranged in this embodiment about a central axis 84 of the through-port chamber 60. Other arrangements are also contemplated. The through-port chamber 60 is a substantially hollow chamber configured to allow liquid to flow from the proximal hub 68 end to the distal hub 62 end or vice versa. Attached to the distal hub 62 is a male luer locking hub 90, and attached to the proximal hub 68 is a female luer locking port 94. FIG. 4A illustrates an exploded view with the male luer locking hub 90 and the female luer locking port 94 being separate from the through-port chamber 60. Luer locking ports are depicted and described in the present disclosure for brevity; however, other orientations and other types of ports are also contemplated.

The distal hub 62 of the through-port chamber 60 includes a distal hub shoulder 64 and a distal hub shoulder counter bore 66. The distal hub shoulder 64 and a distal hub shoulder counter bore 66 are configured to accept and connect to the male luer locking hub 90, with a male luer tip 92 of the male luer locking hub 90 being opposite of the through-port chamber 60. The male luer locking hub 90 is configured to connect to a needle 24 (not illustrated in FIG. 4A).

The proximal hub 68 of the through-port chamber 60 includes a proximal hub shoulder 70 and a proximal hub shoulder counter bore 72. The proximal hub shoulder 70 and the proximal hub shoulder counter bore 72 are configured to accept and connect to the female luer locking port 94, with a female luer locking ring 96 of the female luer locking port 94 being opposite of the through-port chamber 60. The female luer locking port is configured to connect to a syringe 20 (not illustrated in FIG. 4A).

The through-port chamber 60 also includes a plurality of circuit assembly mounting posts 76a-76d on an outside of the chamber. These plurality of circuit assembly mounting posts 76a-76d are configured to align with at least a subset of the mounting holes 38a-38d of the circuit assembly 26 (shown in FIG. 3A), such that the through-port body 28 aligns with the circuit assembly 26.

The carrier body 58 of the through-port body 28 includes a plurality of mounting holes 74a-74c, a battery well 80, and a plurality of battery stack support bosses 78a-78c. The plurality of mounting holes 74a-74c are configured to accept pins or support bosses to align the through-port body 28 (along with the circuit assembly 26) with a housing 30 (not illustrated in FIG. 4A) of the needle-position-tracking element 22. The battery well 80 and the plurality of battery stack support bosses 78a-78c are together configured to contain or house one or more batteries (not illustrated in FIG. 4A) in position to electrically contact the battery contacts 48a-48b (not illustrated in FIG. 4A) of the circuit assembly 26 (not illustrated in FIG. 4A), which is shown in FIG. 5C.

Because a drug or other liquid is passing through the through-port chamber 60, the through-port body 28 needs to be discarded or sanitized for future use. Thus, one advantage of the through-port body 28 being separate from the circuit assembly 26 (described herein) is that, after use of the medical instrument 16, the through-port body 28 can be either discarded or cleaned and sterilized.

FIGS. 4B and 4C illustrate additional views of the through-port body 28. For ease of illustration, however, the male luer locking hub 90 and the female luer locking port 94 are not shown in these figures. FIG. 4B is side view of the through-port body 28, and FIG. 4C is a cross-sectional view of the through-port body 28 from section B-B illustrated in FIG. 4B.

Figure 5A:
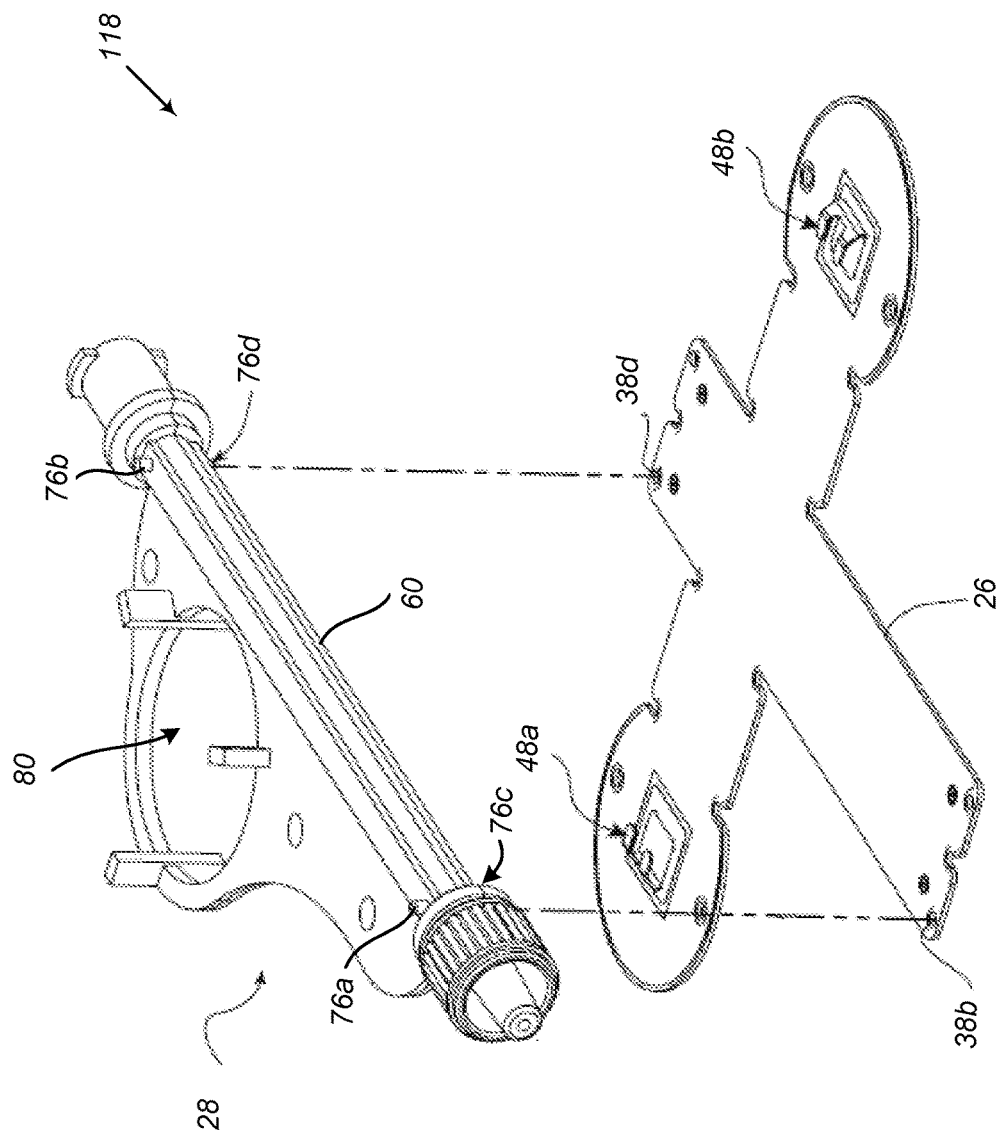
FIGS. 5A-5D are illustrations of the assembly of the circuit assembly and the through-port body of the needle-position-tracking element, according to one embodiment.
Figure 5B:
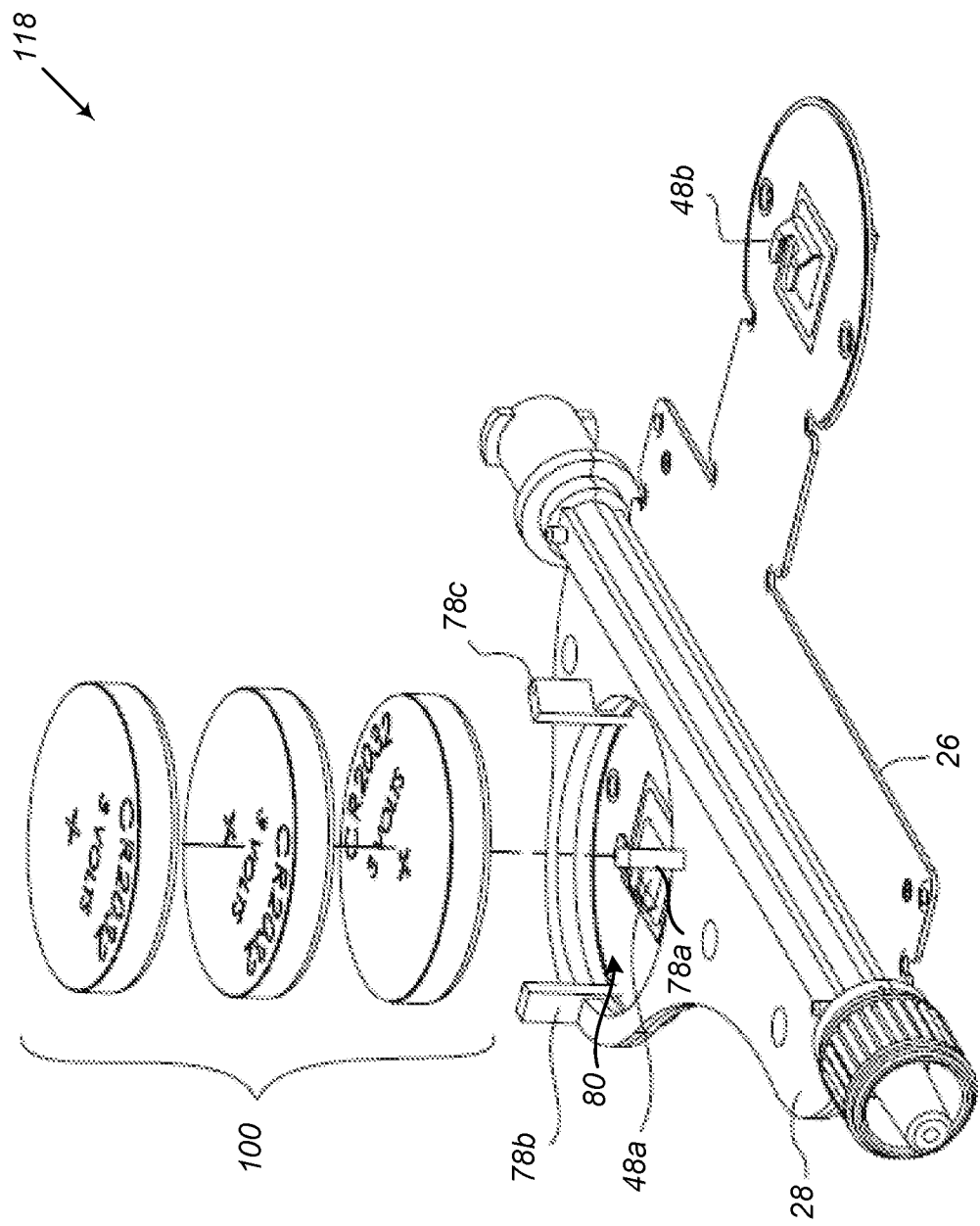
Figure 5C:
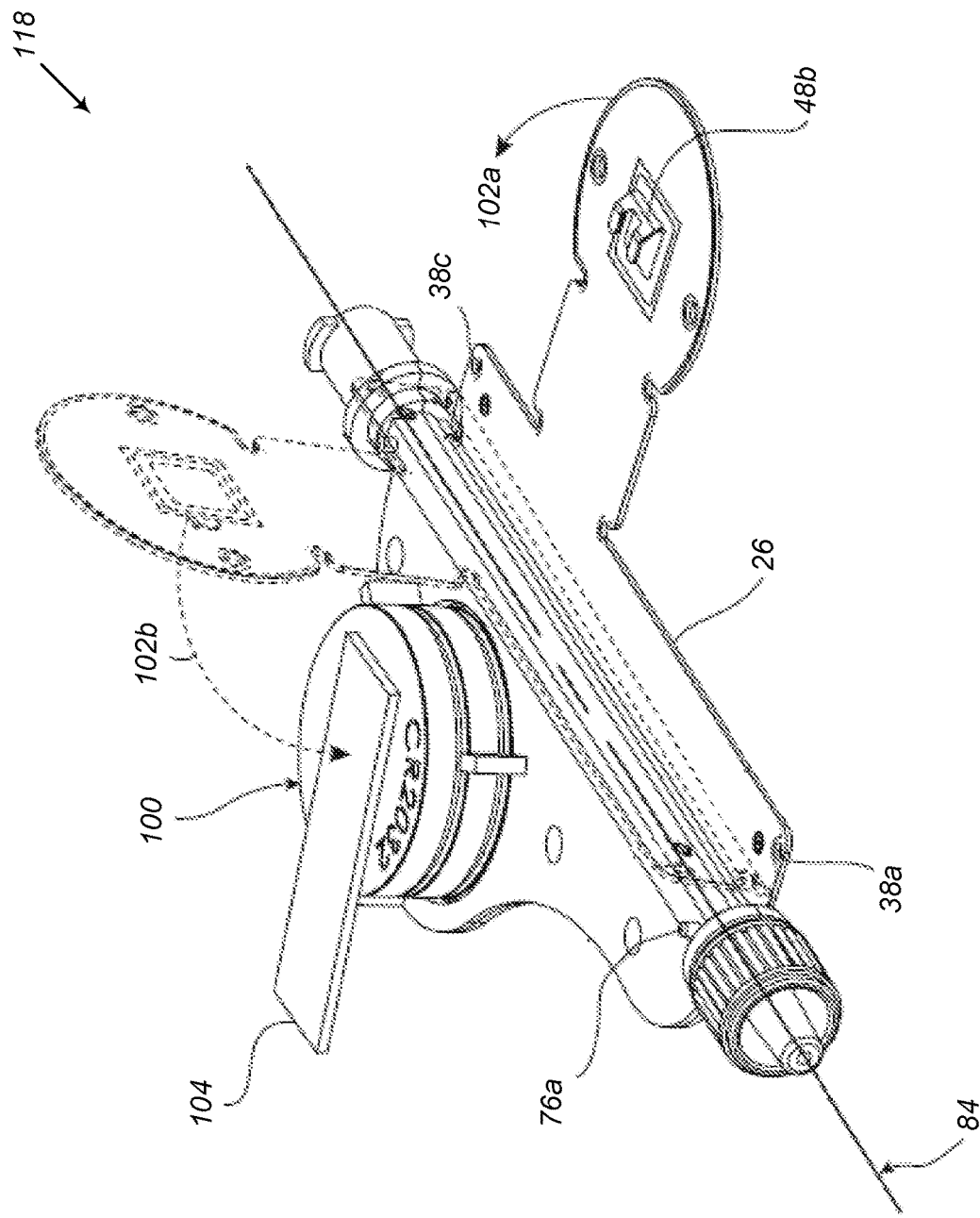
Figure 5D:
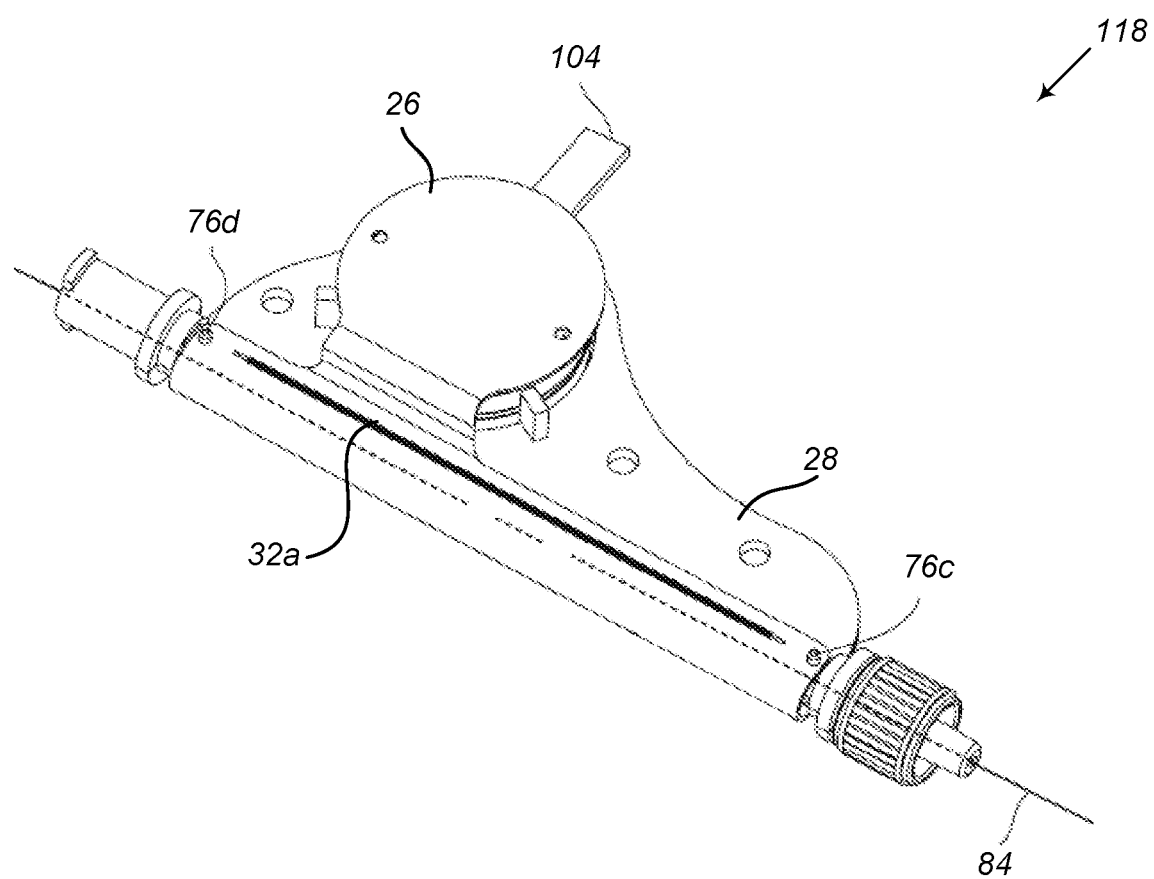
Figure 6A:
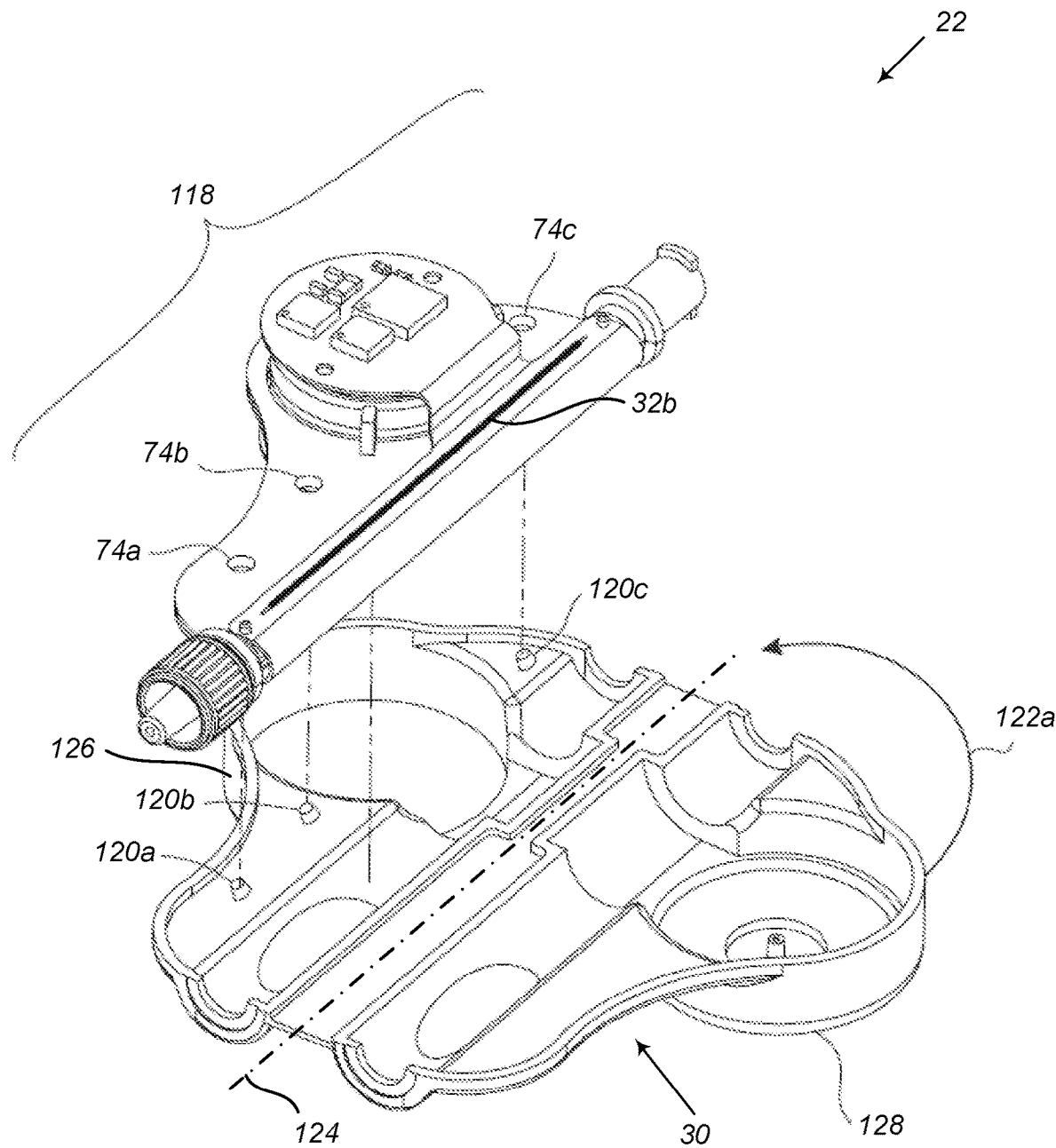
FIGS. 6A-6D are illustrations of the needle-position-tracking element having the circuit assembly and through-port assembly in a housing, according to one embodiment.
Figure 6B:
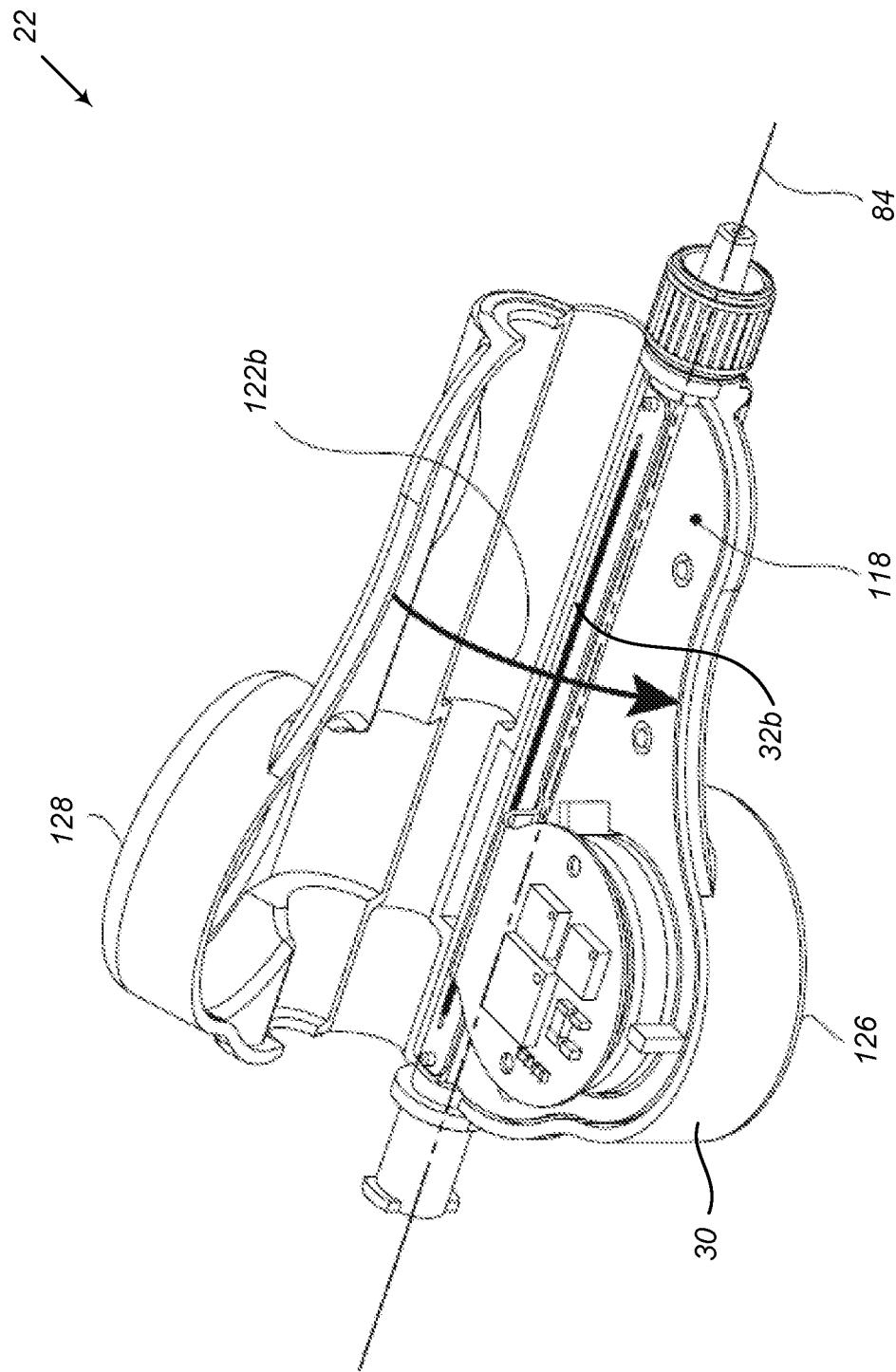
Figure 6C:
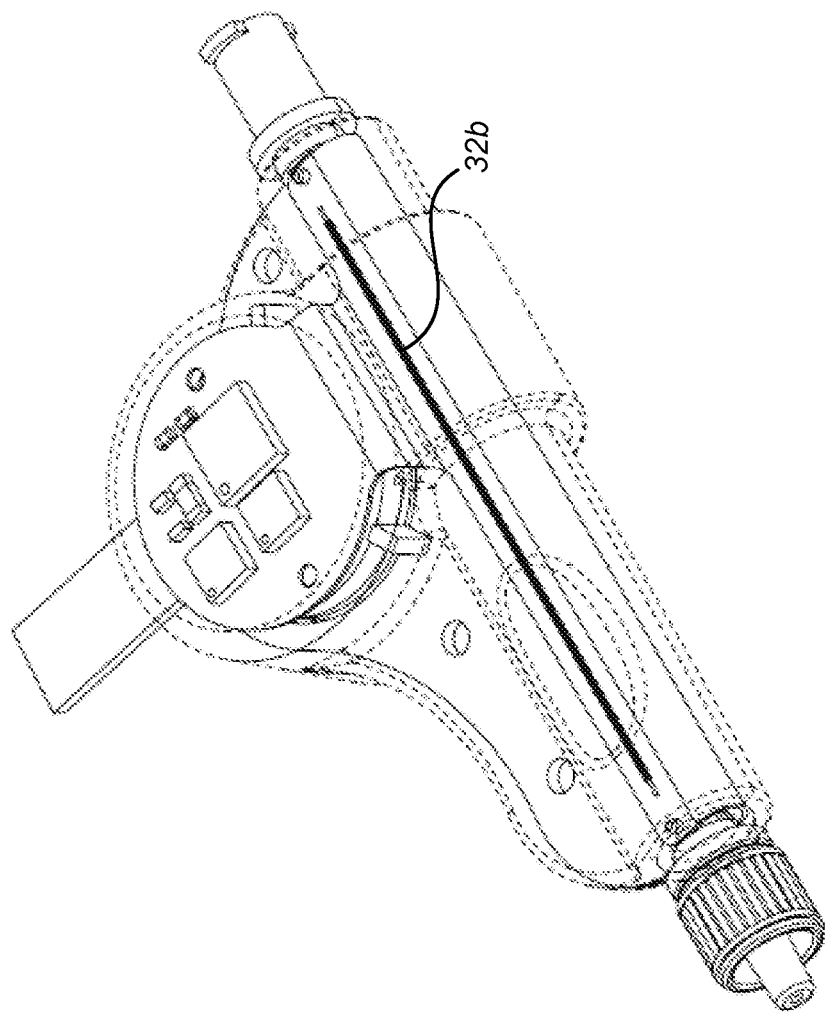
Figure 6D:
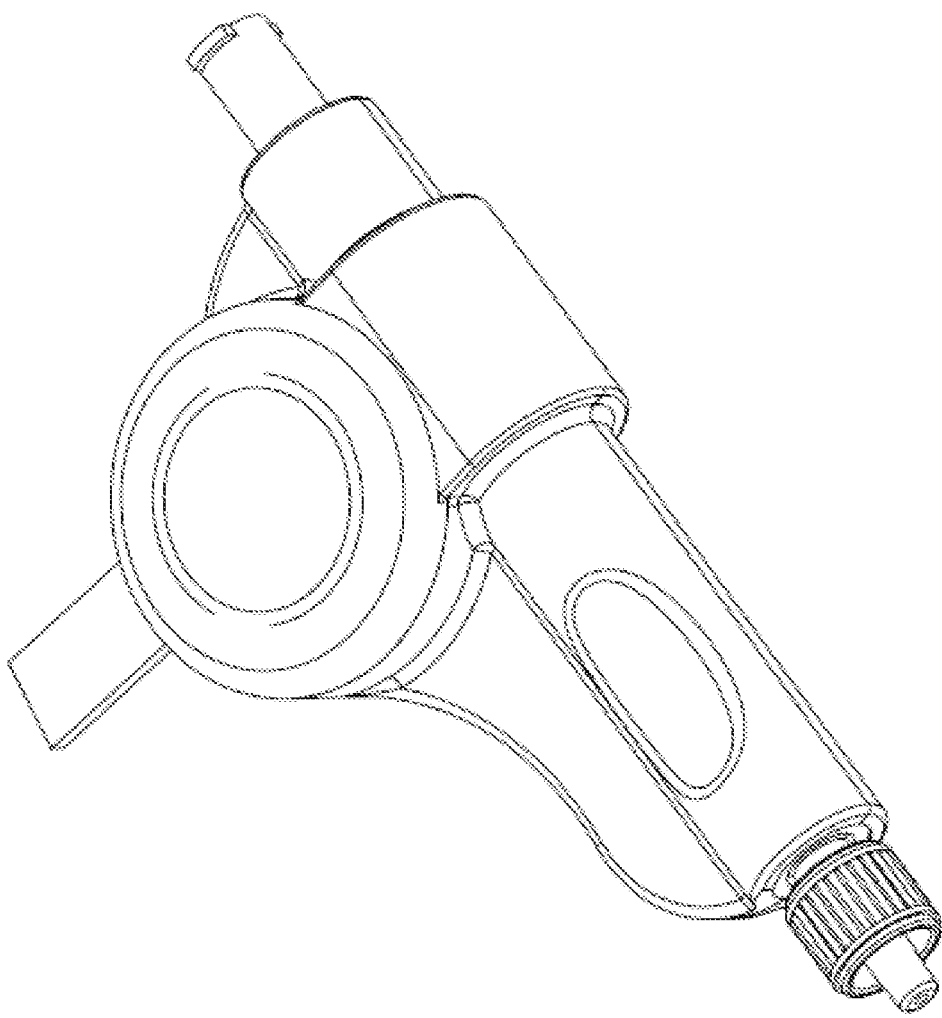

FIGS. 5A-5D are illustrations of the assembly 118 of the circuit assembly 26 and the through-port body 28 of the needle-position-tracking element 22 (FIG. 2), according to one embodiment. In some embodiments, the circuit assembly 26 includes a plurality of mounting holes 38a-38d and the through-port body 28 includes a plurality of circuit assembly mounting posts 76a-76d, which are utilized to align and stabilize the circuit assembly 26 with the through-port body 28. For example, the mounting post 76c on the through-port body 28 aligns with the mounting hole 38b on the circuit assembly 26, and the mounting post 76d on the through-port body 28 aligns with the mounting hole 38d on the circuit assembly 26, as shown in FIGS. 5A-5B.

When the mounting posts 76c and 76d are positioned in and engaged with the mounting holes 38b and 38d, respectively, the battery contact 48a on the circuit assembly 26 is centrally positioned adjacent to the battery well 80 on the through-port body 28. In this way, one or more batteries 100 can be positioned in the battery well 80 to be in electrical contact with the battery contact 48a, as illustrated in FIGS. 5B and 5C.

Once batteries 100 are positioned in battery well 80, the circuit assembly 26 is folded around the through-port chamber 60 of the through-port body 28 about the central axis 84 of the through-port chamber 60, such that the battery contact 48b on the circuit assembly 26 is centrally positioned adjacent to the battery well 80 on the through-port body 28 opposite of the battery contact 48a. Once folded, the mounting post 76a on the through-port body 28 aligns and engages with the mounting hole 38a on the circuit assembly 26, and the mounting post 76b on the through-port body 28 aligns and engages with the mounting hole 38c on the circuit assembly 26. FIG. 5C illustrates this folding of the circuit assembly 26 along folding paths 102a-102b, resulting in the circuit and through-port assembly 118, which is shown in FIGS. 5A-5D. In one embodiment, the electromagnet structures 32a-32b are parallel to the through-port chamber 60.

In some embodiments, the circuit and through-port assembly 118 includes a battery-contact insulation strip 104. The battery-contact insulation strip 104 is positioned between the batteries 100 and one of the battery contacts 48a-48b. In this way, the batteries 100 are not in electrical contact with both battery contacts 48a-48b until the battery-contact insulation strip 104 is removed by a medical practitioner prior to use. Thus, the battery-contact insulation strip 104 may be arranged to act as an "on" switch to power the ancillary circuitry and initiate the excitation signal through the electromagnet structures on the circuit assembly 26. In other embodiments, the circuit assembly 26 may also include an on/off switch (not illustrated in FIG. 5C).

FIGS. 6A-6D are illustrations of the needle-position-tracking element 22 having the circuit and through-port assembly 118 in a housing 30, according to one embodiment. The housing 30 is shaped and configured to contain the circuit and through-port assembly 118. The housing 30 includes a first housing portion 126 and a second housing portion 128. In one embodiment, the first housing portion 126 is a substantially mirror image of the second housing portion 128, such that the housing 30 can fold along axis 124 in folding direction 122a-122b to encase the circuit and through-port assembly 118. The housing 30 protects the various electrical components of the circuit assembly 26. Moreover, having the housing 30 separate from the circuit and through-port assembly 118 allows for the housing 30 to be either discarded or cleaned and sterilized after use.

In some embodiments, the housing 30, e.g., the first portion of the housing 126, includes a plurality of alignment bosses 120a-120c. The alignment bosses 120a-120c are configured to align with the mounting holes 74a-74c on the through-port body 28, which aligns and secures the circuit and through-port assembly 118 with the housing 30.

Figure 7A:
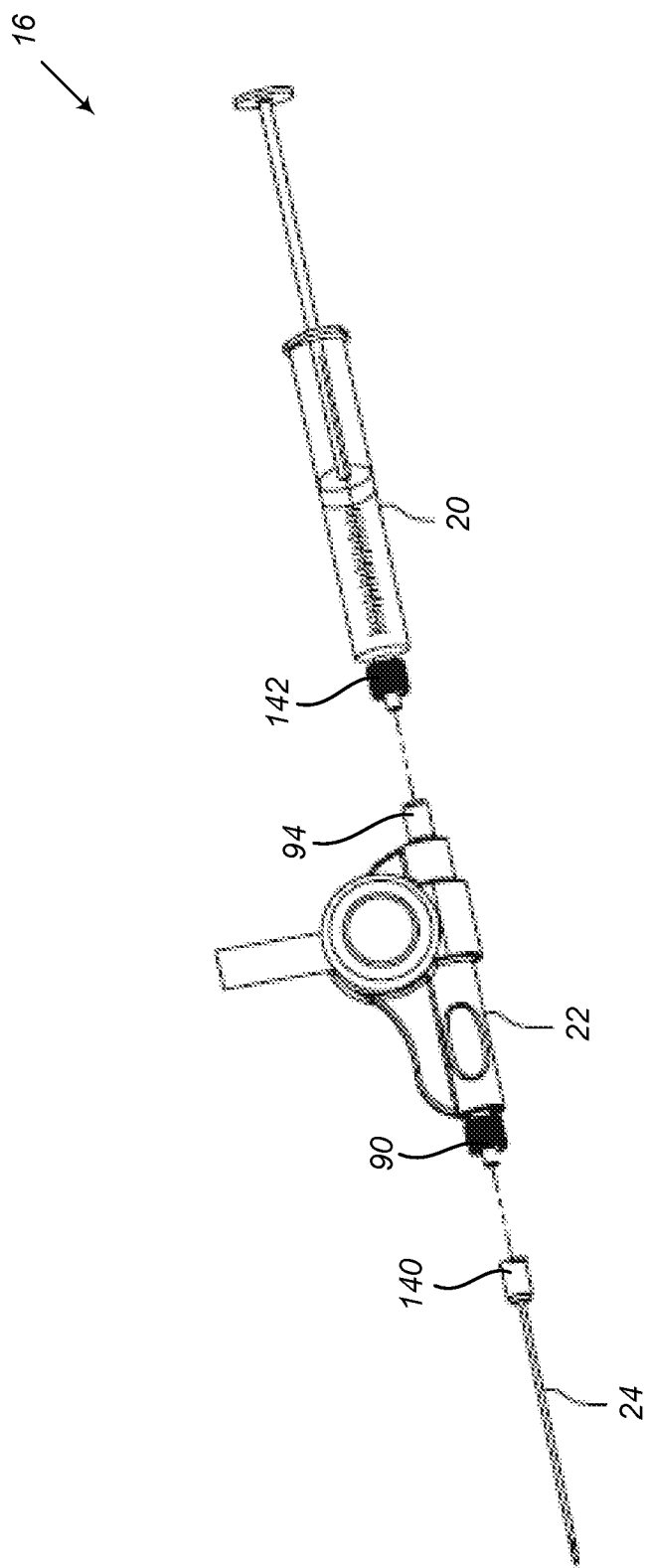
FIGS. 7A-7B are illustrations of the medical instrument having a syringe, a needle, and a needle-position-tracking element, according to one embodiment.
Figure 7B:
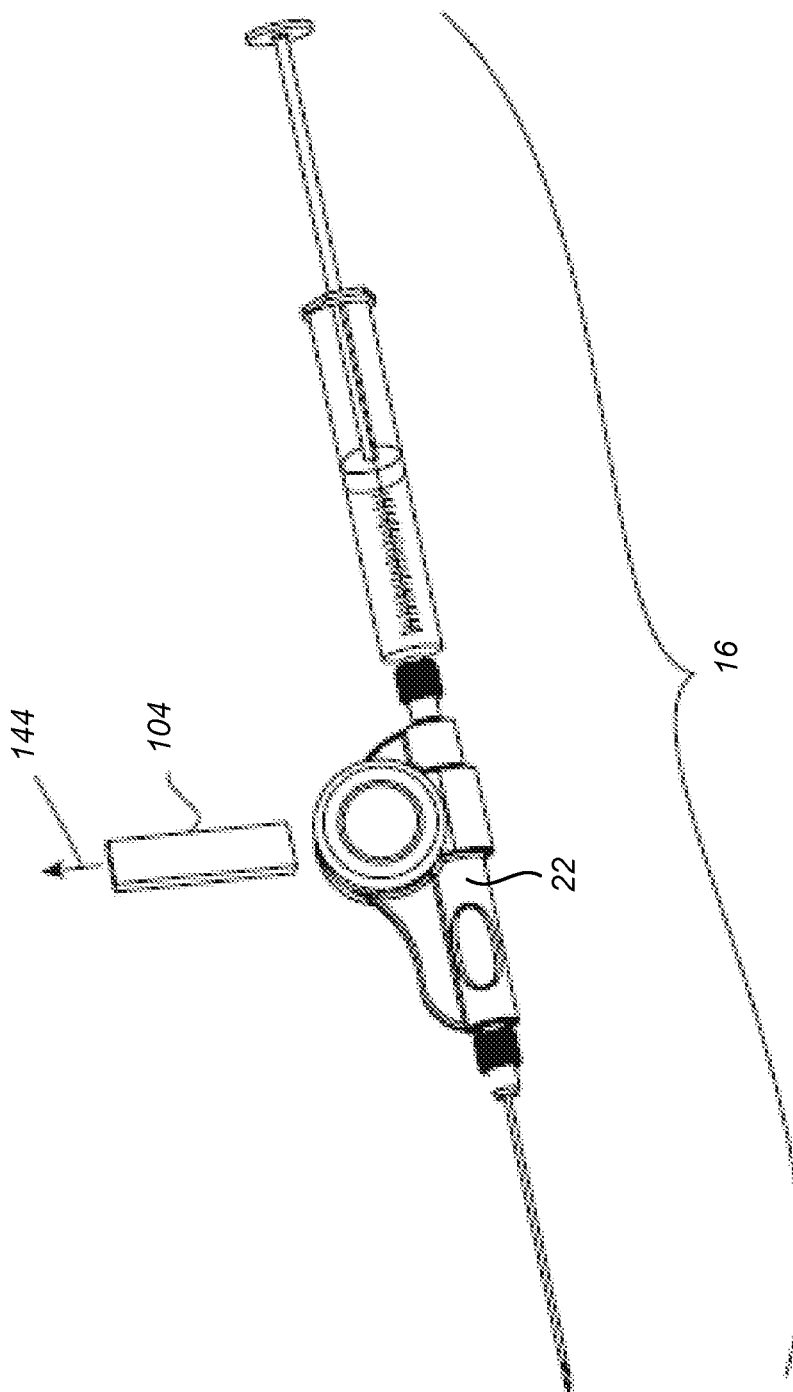

FIGS. 7A-7B are illustrations of the medical instrument 16 having the syringe 20, the needle 24, and the needle-position-tracking element 22, according to one embodiment. As described herein, the needle-position-tracking element 22 includes a male luer locking hub 90 and a female luer locking port 94. A female luer locking port 140 on the needle 24 is configured to connect with the male luer locking hub 90, and a male luer locking hub 142 on the syringe 20 is configured to connect with the female luer locking port 94. In this way, liquid can flow from the syringe 20, through the needle-position-tracking element 22, through the needle 24, and into the body of a patient (e.g., during a liquid inducing medical procedure), or in the opposite direction depending on the needle and syringe configuration (e.g., during a blood draw procedure).

When a medical practitioner is ready to use the medical instrument 16, the medical practitioner removes the battery-contact insulation strip 104 in the removal direction 144, which completes the circuit and initiates the circuitry to drive an excitation signal through one or more electromagnet structures in the needle-position-tracking element 22. In some embodiments, one or more sensors detect magnetic field information generated from the electromagnet structures and determine a location of the needle-position-tracking element 22, and thus a position of the needle 24. The position of the needle 24 can be combined with other information to generate a visual representation of the needle 24 in the patient, or the position of the entire medical instrument 16 relative to the patient.

In various embodiments, the needle 24 is a straight needle with a length along its central bore, as illustrated in FIGS. 7A-7B, such that the electromagnet structures in the needle-position-tracking element are parallel to the length of the needle. Embodiments, however, are not so limited, and other shapes of needles may also be utilized. In some embodiments, a medical practitioner may input the type, shape, or other characteristics of the needle into the control circuit 14 (FIG. 1), so that an accurate position of the needle or a portion thereof can be approximated based on the position of the needle-position-tracking element 22 and the relative position and characteristics of the needle 24.

In various embodiments, the syringe is a plunger-style syringe, as illustrated in FIGS. 7A-7B. Embodiments, however, are not so limited, and other styles of syringes or liquid dispensing or liquid extracting medical devices may be used.

Certain words and phrases used in the specification are set forth as follows. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation; such a device may be implemented in hardware, firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

A processor (i.e., a processing unit), as used in the present disclosure, refers to one or more processing units individually, shared, or in a group, having one or more processing cores (e.g., execution units), including central processing units (CPUs), digital signal processors (DSPs), microprocessors, micro controllers, state machines, and the like that execute instructions. In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files.

The files may include functions, services, libraries, and the like. The files may include one or more computer programs or may be part of a larger computer program. Alternatively, or in addition, each file may include data or other computational support material useful to carry out the computing functions of the systems, methods, and apparatus described in the present disclosure. Some or all of the stored contents of a memory may include software instructions executable by a processing device to carry out one or more particular acts.

The terms "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis. An example of an activity that is not real-time is one that occurs over an extended period of time (e.g., hours or days) or that occurs based on intervention or direction by a person or other activity, such as each magnetic sense measurement occurring at the press of a button.

Unless the context requires otherwise, throughout the specification and claims which follow, the word "comprise" and variations thereof, such as "comprises" and "comprising," are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

Where the terms "substantial" or "about" in any grammatical form are used as modifiers in the present disclosure and any appended claims (e.g., to modify a structure, a dimension, a measurement, or some other characteristic), it is understood that the characteristic may vary by up to 30 percent. For example, a length of an electromagnet structure may be described as substantially parallel to a length of a needle. In these cases, the vector describing the orientation of the electromagnet can be decomposed into a part parallel to the needle and a part transverse. The magnitude of the transverse part would not exceed the magnitude of the parallel part by more than 30 percent. By the application of trigonometry, this suggests that the angle between the electromagnet and then needle, if they were moved to have the same starting point, would not exceed 17 degrees.

The headings and Abstract of the Disclosure provided herein are for convenience only and do not limit or interpret the scope or meaning of the embodiments.

The various embodiments described herein can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
   a medical instrument;
   a magnetic field generator configured to operatively couple to the medical instrument, the magnetic field generator including:
   a needle-position-tracking element having a through-port body that is arranged for fluid communication between a syringe and a needle, a circuit assembly proximal to the through-port body, and a housing that contains the through-port body and the circuit assembly, the circuit assembly including:
   a first electromagnet structure having a first core and a first conductive coil wound around the first core;
   a second electromagnet structure having a second core and a second conductive coil wound around the second core, the first electromagnet structure and the second electromagnet structure having a length substantially parallel to a length of the needle when the needle is arranged in fluid communication with the through-port body; and
   ancillary circuitry electrically coupled to the first conductive coil and the second conductive coil, the ancillary circuitry configured to controllably drive a first excitation signal through the first conductive coil to thereby generate a first magnetic field about the first electromagnet structure, and further configured to controllably drive a second excitation signal through the second conductive coil to thereby generate a second magnetic field about the second electromagnet structure,
   wherein the first excitation signal is different from the second excitation signal and the first magnetic field is different from the second magnetic field, and
   wherein the ancillary circuitry generates location information of the needle based on the first magnetic field and the second magnetic field.

2. The system of claim 1, wherein the medical instrument further comprises:
   a needle having an internal bore, the needle structured for at least partial insertion into a body of a patient, the needle structured to transfer a substance to or from the body of the patient; and
   a syringe having a first chamber to contain the substance.

3. The system of claim 2, further comprising:
   a sensor device configured to sense the first magnetic field generated when the first excitation signal is driven through the first conductive coil and further configured to generate a sensor signal representative of at least one portion of the sensed first magnetic field; and
   a control circuit configured to calculate information corresponding to a position of the needle within the body of the patient based on the sensor signal.

4. The system of claim 3, wherein the control circuit configured to calculate the information corresponding to the position of the needle within the body of the patient is further configured to:
   determine a position of the first electromagnet structure from the sensor signal; and
   determine the position of the needle based on the position of the first electromagnet structure and further based on a known positional relationship of the needle relative to the first electromagnet structure.

5. The system of claim 2, wherein the through-port body includes a carrier body and a through-port chamber, the carrier body having at least one mounting hole for securely aligning the through-port body to the housing, wherein the through-port chamber is structured to permit a transfer of a liquid through the needle-position-tracking element between the syringe and the needle.

6. The system of claim 5, wherein the through-port chamber is adjacent and substantially parallel to the first and second electromagnet structures.

7. The system of claim 2, further comprising:
   a first female luer locking port integrated with the needle;
   a first male luer locking hub integrated with the syringe;
   a second male luer locking hub integrated with the through-port body and connected to the first female luer locking port of the needle; and
   a second female luer locking port integrated with the through-port body and connected to the first male luer locking port of the syringe.

8. The system of claim 2, wherein the substance is a liquid.

9. The system of claim 2, wherein the substance is a non-liquid.

10. The system of claim 1, wherein the circuit assembly includes a flexible portion arranged around the through-port body.

11. The system of claim 1, wherein
    the second electromagnet structure is arranged substantially parallel to the first electromagnet structure.

12. The system of claim 1, wherein the through-port body contains at least one battery arranged to supply power to the ancillary circuitry.

13. A system, comprising:
    a medical instrument, the medical instrument including:
    a needle-position-tracking element having a through-port body that is arranged for fluid communication between a syringe and a needle, a circuit assembly proximal to the through-port body, and a housing that contains the through-port body and the circuit assembly, the circuit assembly including:
    an electromagnet structure having a length substantially parallel to a length of the needle when the needle is arranged in fluid communication with the through-port body, the electromagnet structure having a core and a conductive coil wound around the core; and
    ancillary circuitry electrically coupled to the conductive coil, the ancillary circuitry configured to controllably drive an excitation signal through the conductive coil to thereby generate a magnetic field about the electromagnet structure;
    a plurality of mounting posts integrated with the through-port body; and
    a plurality of mounting holes integrated in the circuit assembly, the plurality of mounting holes engaging the plurality of mounting posts to secure the circuit assembly to the through-port body.

14. The system of claim 13, wherein the communication is a fluid communication.

15. The system of claim 13, wherein the communication is a liquid communication.

16. The system of claim 13, wherein the communication is a mechanical communication.

17. The system of claim 13, wherein the communication is an electrical communication.

18. A medical device, including:
a through-port body having a first locking structure at a first end, a second locking structure at a second end opposite of the first end, and a through-port chamber that is in communication between the first locking structure and the second locking structure, the through-port chamber having a central axis;
a circuit assembly proximal to the through-port body, the circuit assembly including:
a first electromagnet structure formed with a first core and a first conductive coil wound around the first core, the first core being substantially parallel to the central axis;
a second electromagnet structure formed with a second core and a second conductive coil wound around the second core, the second core being substantially parallel to the central axis; and
ancillary circuitry electrically coupled to the first conductive coil and the second conductive coil, the ancillary circuitry configured to drive a first excitation signal through the first conductive coil to thereby generate a first magnetic field about the first electromagnet structure and further configured to drive a second excitation signal through the second conductive coil to thereby generate a second magnetic field about the second electromagnet structure, the first excitation signal being different from the second excitation signal; and
a housing that contains the through-port body and the circuit assembly,
wherein the ancillary circuitry generates location information of the needle based on the first magnetic field and the second magnetic field.

19. The medical device of claim 18, wherein the first locking structure is a luer locking hub and wherein the second locking structure is a luer locking port.

20. The medical device of claim 18, wherein the first locking structure is a male luer locking hub and wherein the second locking structure is a female luer locking port.

21. The medical device of claim 18, wherein the first locking structure of the through-port body is arranged for connection to a needle having a first cooperative locking structure, and wherein the second locking structure of the through-port body is arranged for connection to a syringe having a second cooperative locking structure.

22. The medical device of claim 21, wherein the first and second locking structures and the first and second cooperative locking structures are arranged according to a luer locking structure.

23. The medical device of claim 21, wherein each of the first and second electromagnet structures have a length that is substantially parallel to the needle when the through-port body is connected to the needle having the first cooperative locking structure.

24. The medical device of claim 21, wherein each of the first and second electromagnet structures have a length that is substantially parallel to the through-port chamber.

25. The medical device of claim 18, wherein the through-port body includes:
a battery well to house at least one battery.

26. A medical device, including:
a through-port body having a first locking structure at a first end, a second locking structure at a second end opposite of the first end, and a through-port chamber between the first locking structure and the second locking structure;
a circuit assembly proximal to the through-port body, the circuit assembly including:
an electromagnet structure formed with a core and a conductive coil wound around the core; and
ancillary circuitry electrically coupled to the conductive coil, the ancillary circuitry configured to drive an excitation signal through the conductive coil to thereby generate a magnetic field about the electromagnet structure; and
a housing that contains the through-port body and the circuit assembly, wherein the circuit assembly includes:
a first portion having a first battery contact that is electrically coupled to the ancillary circuitry;
a second portion having a second battery contact that is electrically coupled to the ancillary circuitry; and
a flexible third portion disposed between the first and second portions to at least partially wrap the circuit assembly around the through-port chamber and thereby arrange the first portion substantially parallel to the second portion and further arrange the first battery contact opposite to the second battery contact.

27. A medical device, including:
a through-port body having a first locking structure at a first end, a second locking structure at a second end opposite of the first end, and a through-port chamber between the first locking structure and the second locking structure;
a circuit assembly proximal to the through-port body, the circuit assembly including:
an electromagnet structure formed with a core and a conductive coil wound around the core; and
ancillary circuitry electrically coupled to the conductive coil, the ancillary circuitry configured to drive an excitation signal through the conductive coil to thereby generate a magnetic field about the electromagnet structure; and
a housing that contains the through-port body and the circuit assembly, wherein the through-port body includes:
a carrier body having at least one mounting hole arranged to align and secure the through-port body to the housing.

28. A medical device, including:
a through-port body having a first locking structure at a first end, a second locking structure at a second end opposite of the first end, and a through-port chamber between the first locking structure and the second locking structure;
a circuit assembly proximal to the through-port body, the circuit assembly including:
an electromagnet structure formed with a core and a conductive coil wound around the core; and
ancillary circuitry electrically coupled to the conductive coil, the ancillary circuitry configured to drive an excitation signal through the conductive coil to thereby generate a magnetic field about the electromagnet structure;
a housing that contains the through-port body and the circuit assembly;

a plurality of mounting posts integrated in the through-port body; and
a plurality of mounting holes integrated in the circuit assembly, wherein the plurality of mounting holes are arranged to engage the plurality of mounting posts to secure the circuit assembly to the through-port body.

* * * * *